(12) United States Patent
Truckal et al.

(10) Patent No.: US 7,354,440 B2
(45) Date of Patent: Apr. 8, 2008

(54) ELECTROSURGICAL INSTRUMENT AND METHOD OF USE

(75) Inventors: Csaba Truckal, Saratoga, CA (US); John H. Shaddock, Tiburon, CA (US)

(73) Assignee: SurgRx, Inc., Redwood City, CA (US)

( * ) Notice: Subject to any disclaimer, the term of this patent is extended or adjusted under 35 U.S.C. 154(b) by 597 days.

(21) Appl. No.: 10/993,413

(22) Filed: Nov. 18, 2004

(65) Prior Publication Data

US 2005/0171535 A1     Aug. 4, 2005

Related U.S. Application Data

(63) Continuation-in-part of application No. 10/934,755, filed on Sep. 3, 2004, now Pat. No. 7,189,233, which is a continuation-in-part of application No. 10/032,867, filed on Oct. 22, 2001, now Pat. No. 6,929,644.

(60) Provisional application No. 60/563,424, filed on Apr. 19, 2004, provisional application No. 60/523,567, filed on Nov. 19, 2003, provisional application No. 60/500,746, filed on Sep. 4, 2003.

(51) Int. Cl.
*A61B 18/12*     (2006.01)

(52) U.S. Cl. .......................................... 606/51; 606/41

(58) Field of Classification Search ............. 606/41–49
See application file for complete search history.

(56) References Cited

U.S. PATENT DOCUMENTS 659,409 A     10/1900     Mosher (Continued)

FOREIGN PATENT DOCUMENTS

EP     341 446 A2     4/1989

(Continued)

OTHER PUBLICATIONS

Corson, S.L., "Two new laparoscopic instruments: Bipolar sterilizing forceps and uterine manipulator," *Medical Instrumentation*, 11(1):7-8 (1977).

(Continued)

*Primary Examiner*—Michael Peffley
*Assistant Examiner*—Aaron Roane
(74) *Attorney, Agent, or Firm*—Townsend and Townsend and Crew LLP

(57) ABSTRACT

Embodiments of the invention provide an electrosurgical jaw structure comprising first and second opposing jaws one or both of which include 3D variable resistance bodies. The jaw structure can be part of the working end of a surgical instrument. In one embodiment, the jaws can comprise first and second energy-delivery jaw surfaces having first and second 3D variable resistance bodies, with the jaw surface configured to be coupled to an Rf source. The 3D variable resistance bodies can define different temperature-resistance curves. The 3D bodies can be configured to control ohmic heating of tissue by modulating the delivery of Rf energy to tissue. Jaw structures having the 3D bodies can be used to engage and produce high strength tissue welds in targeted tissue including tissue volumes having varying tissue types. Such jaw structures can be configured to simultaneously apply different energy levels to each tissue type within the tissue volume.

2 Claims, 19 Drawing Sheets

U.S. PATENT DOCUMENTS

| | | |
|---|---|---|
| 1,586,645 A | 6/1926 | Bierman |
| 1,798,902 A | 3/1931 | Raney |
| 1,881,250 A | 10/1932 | Tomlinson |
| 2,031,682 A | 2/1936 | Wappler et al. |
| 3,651,811 A | 3/1972 | Hildebrandt et al. |
| 3,685,518 A | 8/1972 | Beuerle et al. |
| 3,730,188 A | 5/1973 | Ellman |
| 3,768,482 A | 10/1973 | Shaw |
| 3,826,263 A | 7/1974 | Cage et al. |
| 4,092,986 A | 6/1978 | Schneiderman |
| 4,198,957 A | 4/1980 | Cage et al. |
| 4,219,025 A | 8/1980 | Johnson |
| 4,231,371 A | 11/1980 | Lipp |
| 4,232,676 A | 11/1980 | Herczog |
| 4,271,838 A | 6/1981 | Lasner et al. |
| 4,353,371 A | 10/1982 | Cosman |
| 4,370,980 A | 2/1983 | Lottick |
| 4,375,218 A | 3/1983 | DiGeronimo |
| 4,492,231 A | 1/1985 | Auth |
| 4,590,934 A | 5/1986 | Malis et al. |
| 4,608,981 A | 9/1986 | Rothfuss et al. |
| 4,633,874 A | 1/1987 | Chow et al. |
| 4,655,216 A | 4/1987 | Tischer |
| 4,671,274 A | 6/1987 | Sorochenko |
| 4,691,703 A | 9/1987 | Auth et al. |
| 4,763,669 A | 8/1988 | Jaeger |
| 4,785,807 A | 11/1988 | Blanch |
| 4,848,337 A | 7/1989 | Shaw et al. |
| 4,850,353 A | 7/1989 | Stasz et al. |
| 4,887,612 A | 12/1989 | Esser et al. |
| 4,940,468 A | 7/1990 | Petillo |
| 4,958,539 A | 9/1990 | Stasz et al. |
| 4,969,885 A | 11/1990 | Farin |
| 4,985,030 A | 1/1991 | Melzer et al. |
| 5,009,656 A | 4/1991 | Reimels |
| 5,057,106 A | 10/1991 | Kasevich et al. |
| 5,057,107 A | 10/1991 | Parins et al. |
| 5,085,659 A | 2/1992 | Rydell |
| 5,104,025 A | 4/1992 | Main et al. |
| 5,122,137 A | 6/1992 | Lennox |
| 5,147,356 A | 9/1992 | Bhatta |
| 5,147,357 A | 9/1992 | Rose et al. |
| 5,151,102 A | 9/1992 | Kamiyama et al. |
| 5,190,541 A | 3/1993 | Abele et al. |
| 5,201,900 A | 4/1993 | Nardella |
| 5,207,691 A | 5/1993 | Nardella |
| 5,258,006 A | 11/1993 | Rydell et al. |
| 5,267,998 A | 12/1993 | Hagen |
| 5,269,780 A | 12/1993 | Roos |
| 5,290,286 A | 3/1994 | Parins |
| 5,306,280 A | 4/1994 | Bregen et al. |
| 5,308,311 A | 5/1994 | Eggers et al. |
| 5,324,289 A | 6/1994 | Eggers |
| 5,336,221 A | 8/1994 | Anderson |
| 5,360,428 A | 11/1994 | Hutchinson, Jr. |
| 5,364,389 A | 11/1994 | Anderson |
| 5,389,098 A | 2/1995 | Tsuruta et al. |
| 5,403,312 A | 4/1995 | Yates et al. |
| 5,417,687 A | 5/1995 | Nardella et al. |
| 5,443,463 A | 8/1995 | Stern et al. |
| 5,445,638 A | 8/1995 | Rydell et al. |
| 5,451,224 A | 9/1995 | Goble et al. |
| 5,458,598 A | 10/1995 | Feinberg et al. |
| 5,480,397 A | 1/1996 | Eggers et al. |
| 5,480,398 A | 1/1996 | Eggers |
| 5,507,106 A | 4/1996 | Fox |
| 5,531,744 A | 7/1996 | Nardella et al. |
| 5,571,153 A | 11/1996 | Wallsten |
| 5,573,535 A | 11/1996 | Viklund |
| 5,593,406 A | 1/1997 | Eggers et al. |
| 5,611,798 A | 3/1997 | Eggers |
| 5,624,452 A | 4/1997 | Yates |
| 5,674,220 A | 10/1997 | Fox et al. |
| 5,693,051 A | 12/1997 | Schulze et al. |
| 5,716,366 A | 2/1998 | Yates |
| 5,735,848 A | 4/1998 | Yates et al. |
| 5,755,717 A | 5/1998 | Yates et al. |
| 5,766,166 A | 6/1998 | Hooven |
| 5,776,130 A | 7/1998 | Buysse et al. |
| 5,797,938 A | 8/1998 | Paraschal et al. |
| 5,800,449 A | 9/1998 | Wales |
| 5,807,392 A | 9/1998 | Eggers |
| 5,833,690 A | 11/1998 | Yates et al. |
| 5,911,719 A | 6/1999 | Eggers |
| 5,947,984 A | 9/1999 | Whipple |
| 6,019,758 A | 2/2000 | Slater |
| 6,030,384 A | 2/2000 | Nezhat |
| 6,039,733 A | 3/2000 | Buysse et al. |
| 6,074,389 A | 6/2000 | Levine et al. |
| 6,086,586 A | 7/2000 | Hooven |
| 6,113,598 A | 9/2000 | Baker |
| 6,139,508 A | 10/2000 | Simpson et al. |
| 6,152,923 A | 11/2000 | Ryan |
| 6,162,220 A | 12/2000 | Nezhat |
| 6,174,309 B1 | 1/2001 | Wrublewski et al. |
| 6,176,857 B1 | 1/2001 | Ashley |
| 6,179,834 B1 | 1/2001 | Buysse et al. |
| 6,179,835 B1 | 1/2001 | Panescu et al. |
| 6,179,837 B1 | 1/2001 | Hooven |
| 6,187,003 B1 | 2/2001 | Buysse et al. |
| 6,190,386 B1 | 2/2001 | Rydell |
| 6,193,709 B1 | 2/2001 | Miyawaki et al. |
| 6,270,497 B1 | 8/2001 | Sekino et al. |
| 6,273,887 B1 | 8/2001 | Yamauchi et al. |
| 6,277,117 B1 | 8/2001 | Tetzlaff et al. |
| 6,296,640 B1 | 10/2001 | Wampler et al. |
| 6,328,703 B1 | 12/2001 | Murakami |
| 6,334,861 B1 | 1/2002 | Chandler et al. |
| 6,350,264 B1 | 2/2002 | Hooven |
| 6,352,536 B1 | 3/2002 | Buysse et al. |
| 6,398,779 B1 | 6/2002 | Buysse et al. |
| 6,409,725 B1 | 6/2002 | Khandkar et al. |
| 6,451,018 B1 | 9/2002 | Lands et al. |
| 6,458,128 B1 | 10/2002 | Schulze |
| 6,458,130 B1 | 10/2002 | Frazier et al. |
| 6,464,704 B2 | 10/2002 | Schmaltz |
| 6,468,275 B1 | 10/2002 | Wampler et al. |
| 6,500,176 B1 | 12/2002 | Truckai et al. |
| 6,511,480 B1 | 1/2003 | Tetzlaff et al. |
| 6,527,767 B2 | 3/2003 | Wang et al. |
| 6,533,784 B2 | 3/2003 | Truckai et al. |
| 6,554,829 B2 | 4/2003 | Schulze et al. |
| 6,575,968 B1 | 6/2003 | Eggers et al. |
| 6,585,735 B1 | 7/2003 | Frazier et al. |
| 6,632,193 B1 | 10/2003 | Davison et al. |
| 6,652,521 B2 | 11/2003 | Schulze |
| 6,843,789 B2 * | 1/2005 | Goble ......................... 606/41 |
| 6,893,435 B2 * | 5/2005 | Goble ......................... 606/41 |
| 2002/0052599 A1 | 5/2002 | Goble |
| 2002/0115997 A1 | 8/2002 | Truckai et al. |
| 2002/0120266 A1 | 8/2002 | Truckai et al. |
| 2002/0169392 A1 | 11/2002 | Truckai et al. |
| 2002/0177848 A1 | 11/2002 | Truckai et al. |
| 2003/0018327 A1 | 1/2003 | Truckai et al. |
| 2003/0050635 A1 | 3/2003 | Truckai et al. |
| 2003/0055417 A1 | 3/2003 | Truckai et al. |
| 2003/0069579 A1 | 4/2003 | Truckai et al. |
| 2003/0078573 A1 | 4/2003 | Truckai et al. |
| 2003/0078577 A1 | 4/2003 | Truckai et al. |
| 2003/0078578 A1 | 4/2003 | Truckai et al. |
| 2003/0114851 A1 | 6/2003 | Truckai et al. |
| 2003/0125727 A1 | 7/2003 | Truckai et al. |

| | | | |
|---|---|---|---|
| 2003/0139741 A1 | 7/2003 | Goble et al. | |
| 2003/0144652 A1 | 7/2003 | Baker et al. | |

FOREIGN PATENT DOCUMENTS

| | | |
|---|---|---|
| EP | 517 244 B1 | 3/1996 |
| EP | 518 230 B1 | 5/1996 |
| FR | 2536924 A1 | 6/1984 |
| FR | 2647683 A1 | 12/1990 |
| GB | 2037167 A | 7/1980 |
| GB | 2066104 A | 7/1981 |
| GB | 2133290 A | 7/1984 |
| GB | 2161082 A | 1/1986 |
| SU | 342617 | 7/1972 |
| SU | 575103 | 10/1977 |
| WO | WO 93/08754 A1 | 5/1993 |
| WO | WO 94/24949 A1 | 11/1994 |
| WO | WO 94/24951 A1 | 11/1994 |

OTHER PUBLICATIONS

Burton, J.D.K., "New Inventions," *The Lancet*, pp. 650-651 (1959).

Nardella, P.C., "Radio Frequency Energy and Impedance Feedback," *Proc. SPIE. Catheter-Based Sensing and Imaging Technology*, 1068: 42-48 (1989).

Vallfors et al., "Automatically controlled bipolar electrocoagulation—'COA-COMP'," *Neurosurg Rev.*, 187-190 (1984).

* cited by examiner

ELECTROSURGICAL INSTRUMENT AND METHOD OF USE

CROSS-REFERENCES TO RELATED APPLICATIONS

This application claims benefit of priority under 35 USC 119(e) of U.S. Provisional Patent Application Ser. No. 60/523,567, filed Nov. 19, 2003, entitled Electrosurgical Instrument and Method of Use, which is fully incorporated herein by reference. This application also claims benefit of priority under 35 USC 119(e) of U.S. Provisional Patent Application Ser. No. 60/563,424, filed Apr. 19, 2004 entitled Electrosurgical Instrument With PTC Sensing Surface, which is fully incorporated herein by reference.

This application is also a continuation-in-part of U.S. patent application Ser. No: 10/032,867, now issued as U.S. Pat. No. 6,929,644, filed Oct. 22, 2001, entitled Electrosurgical Jaw Structure for Controlled Energy Delivery; Ser. No. 10/934,755, now issued as U.S. Pat. No. 7,189,233, filed Sep. 3, 2004, entitled Electrosurgical Instrument, which claims the benefit of priority of U.S. Provisional application Ser. No. 60/500,746, filed on Sep. 4, 2003, the full disclosures of which are incorporated herein by reference.

This application is also related to co-pending U.S. patent application Ser. No. 10/351,449 filed Jan. 22, 2003, entitled Electrosurgical Instrument and Method of Use which is incorporated herein by reference. This application is also related to concurrently filed U.S. patent application Ser. No. 10/999,210, which is incorporated herein by this reference.

BACKGROUND OF THE INVENTION

Field of the Invention

Embodiments of the invention relate to medical devices and methods and more particularly relate to an electrosurgical jaw structure with at least one impedance matching three-dimensional body within a jaw for causing controlled ohmic heating of engaged tissue, together with multiple circuitry components for intraoperative control of voltage applied to the engaged tissue.

Radiofrequency (Rf) energy has been employed for surgical applications for the last 80 or more years. More recently, Rf and other energy sources such as ultrasound and lasers have been developed to coagulate, seal or join together tissues volumes in open and laparoscopic surgeries. Particular surgical applications relate to sealing blood vessels which contain considerable fluid pressure therein. In general, no instrument working ends using any energy source have proven reliable in creating a "tissue weld" or "tissue fusion" that has very high strength immediately post-treatment. For this reason, the commercially available instruments, typically powered by Rf or ultrasound, are mostly limited to use in sealing small blood vessels and tissues masses with microvasculature therein. Current Rf devices fail to provide seals with substantial strength in various tissues and anatomical structures including anatomic structures having walls with irregular or thick fibrous content, in bundles of disparate anatomic structures, in substantially thick anatomic structures, or in tissues with thick fascia layers (e.g., large diameter blood vessels).

In a basic bi-polar Rf jaw arrangement, each face of opposing first and second jaws comprises an electrode and Rf current flows across the captured tissue between the opposing polarity electrodes. Such prior art Rf jaws that engage opposing sides of tissue typically cannot cause uniform thermal effects in the tissue—whether the captured tissue is thin or substantially thick. As Rf energy density in tissue increases, the tissue surface becomes desiccated and resistant to additional ohmic heating. Localized tissue desiccation and charring can occur almost instantly as tissue impedance rises, which then can result in a non-uniform seal in the tissue. Currently available Rf jaws can cause further undesirable effects by propagating Rf density laterally from the engaged tissue thus causing unwanted collateral thermal injury or damage.

The commercially available Rf sealing instruments typically adopt a "power adjustment" approach to attempt to control Rf flux in tissue wherein a system controller rapidly adjusts the level of total power delivered to the jaws' electrodes in response to feedback circuitry coupled to the electrodes that measures tissue impedance or electrode temperature. Another approach used consists of jaws designs that provide spaced apart of offset electrodes wherein the opposing polarity electrode portions are spaced apart by an insulator material—which may cause current to flow within an extended path through captured tissue rather that simply between opposing electrode surfaces of the first and second jaws. Electrosurgical grasping instruments having jaws with electrically-isolated electrode arrangements in cooperating jaws faces were proposed by Yates et al. in U.S. Pat. Nos. 5,403,312; 5,735,848; and 5,833,690. However, a need exists for electrosurgical instruments which can reliably create high strength seals in one or more anatomical structures including anatomic structures having walls with irregular or thick fibrous content, in bundles of disparate anatomic structures, in substantially thick anatomic structures, or in tissues with thick fascia layers such as larger arteries and veins.

BRIEF SUMMARY OF THE INVENTION

Embodiments of the invention provide novel electrosurgical systems, structures and methods to deliver energy to targeted tissue volumes in a controlled manner to thermally weld or seal targeted tissue. Embodiments of the system allow for a "one-step" welding-transecting procedure wherein the surgeon can contemporaneously (i) engage tissue within a jaw structure (ii) apply Rf energy to the tissue, and (iii) transect the tissue.

In various embodiments, the invention provides an electrosurgical system having a jaw structure that is configured to apply different energy levels across the jaws' engagement surfaces using "smart" materials that modulate the delivery of energy to tissue, without the need for complex feedback circuitry coupled to thermocouples or other sensors in the jaw structure. These materials can include positive temperature coefficient of resistance (PTC) materials which are used to construct three-dimensional (3D) temperature-responsive variable resistance bodies integral to or carried by the jaw structure. Specific embodiments provide an electrosurgical jaw structure having 3D temperature-responsive variable resistance bodies (which can also be variable impedance bodies as is described herein). Jaw structures having these temperature responsive variable impedance bodies can be used to modulate the delivery of Rf energy to create high strength thermal welds or seals in targeted tissues. Such jaw structure can also be used to engage and weld tissue bundles having varying tissue types, (e.g., fat, blood vessels, fascia, etc.). In specific embodiments, jaw structures having 3D temperature-responsive variable resistance bodies can be configured to simultaneously apply different energy levels to each different tissue type.

Many embodiments of the invention provide an electrosurgical jaw structure comprising first and second opposing jaws one or both of which include 3D variable resistance bodies. The jaw structure can be part of the working end of a number surgical instruments known in the art such as surgical forceps or scissors. In one embodiment, the electrosurgical jaws can comprise first and second energy-delivery jaw surfaces having first and second variable resistance bodies, with the jaw surface configured to be coupled in series to an Rf source. The Rf source can utilize the first and second variable resistance bodies to control Rf energy parameters such as voltage and current within engaged tissue. In another embodiment, the electrosurgical jaws can comprise first and second 3D variable resistance bodies or matrices that define different temperature-resistance curves. The 3D variable resistance bodies can be configured to control ohmic heating of tissue by modulating the delivery of Rf energy to tissue. The bodies can be selected based on their resistance curves (e.g., as is shown in FIGS. 4A and 4B) in order to produce a desired level of control of ohmic heating.

Another embodiment provides and electrosurgical jaw structure comprising first and second jaw bodies defining first and second tissue-engaging surfaces, respectively. At least one of the jaw bodies comprises a three-dimensional (3D) matrix of a temperature-responsive variable impedance material for impedance matching with engaged tissue to thereby provide contemporaneous current flow paths through engaged tissue. The 3D matrix is positioned within at least one of the jaw bodies and is configured to modulate current density in the engaged tissue. Also at least one of the tissue engaging surfaces includes opposing polarity conductor regions positioned on the at least one surface. The regions are configured to be coupled to a voltage source such as an Rf source. Also, the 3D matrix can include first and second matrices having different impedance characteristics such as baseline impedance or a temperature impedance response.

Yet another embodiment of the electrosurgical jaw structure comprises first and second jaw bodies defining first and second energy-delivery surfaces with at least one jaw body comprising first and second opposing polarity portions. A temperature-responsive variable impedance body is positioned intermediate the first and second opposing polarity portions. Also, a portion of the variable impedance body can be exposed on one of the first or the second energy delivery surfaces.

In an exemplary embodiment of a method for using a jaw structure having 3D variable impedance bodies, the jaw structure is used to engage tissue and apply Rf energy to the engaged tissue T to cause ohmic heating therein. After the tissue is elevated in temperature, heat is conducted from the engaged tissue back to the variable impedance bodies to thereby elevate temperatures in at least the surfaces region of the body. When the temperature of the matrix material adjacent the ohmically heated tissue is elevated to a selected temperature, the resistance of the matrix material increases significantly. Current flow can be reduced accordingly or even terminated so as to precisely control energy densities in the engaged tissue. In this way, the matrices can be used to produce more uniform heating of tissue and in turn, more uniform welds.

In various embodiments of methods of the invention, the targeted volume of tissue can be uniformly elevated to the temperature needed to denature proteins therein in order to create a more effective "weld" in tissue. To create a "weld" in tissue, collagen, elastin and other protein molecules within an engaged tissue volume can be denatured by breaking the inter- and intra-molecular hydrogen bonds—followed by re-crosslinking on thermal relaxation to create a fused-together tissue mass. It can be easily understood that ohmic heating in tissue—if not uniform—can at best create localized spots of truly "welded" tissue. Such a non-uniformly denatured tissue volume still is "coagulated" and will prevent blood flow in small vasculature that contains little pressure. However, such non-uniformly denatured tissue may not create a seal with significant strength (e.g. leak strength), for example in 2 mm. to 10 mm. arteries that contain high pressures.

Various embodiments of system and methods of the invention relate to creating thermal "welds" or "fusion" within native tissue volumes. The alternative terms of tissue "welding" and tissue "fusion" are used interchangeably herein to describe thermal treatments of a targeted tissue volume that result in a substantially uniform fused-together tissue mass, for example in welding blood vessels that exhibit substantial burst strength immediately post-treatment. The strength of such welds is desirable (i) for permanently sealing blood vessels in vessel transection procedures, (ii) for welding organ margins in resection procedures, (iii) for welding other anatomic ducts wherein permanent closure is required, and also (iv) for vessel anastamosis, vessel closure or other procedures that join together anatomic structures or portions thereof. The welding or fusion of tissue as disclosed herein is to be distinguished from "coagulation", "sealing", "hemostasis" and other similar descriptive terms that generally relate to the collapse and occlusion of blood flow within small blood vessels or vascularized tissue. For example, any surface application of thermal energy can cause coagulation or hemostasis—but does not fall into the category of "welding" as the term is used herein. Such surface coagulation does not create a weld that provides any substantial strength in the affected tissue.

At the molecular level, the phenomena of truly "welding" tissue as disclosed herein may not be fully understood. However, the authors have identified the parameters at which tissue welding can be accomplished. An effective "weld" as disclosed herein results from the thermally-induced denaturation of collagen, elastin and other protein molecules in a targeted tissue volume to create a transient liquid or gel-like proteinaceous amalgam. In one embodiment of a method the invention, this can be achieved by delivering energy to target tissue to provide a selected energy density in the targeted tissue to cause hydrothermal breakdown of intra- and intermolecular hydrogen crosslinks in collagen and other proteins. The denatured amalgam is maintained at a selected level of hydration—without desiccation—for a selected time interval which can be very brief. The targeted tissue volume is maintained under a selected very high level of mechanical compression to insure that the unwound strands of the denatured proteins are in close proximity to allow their intertwining and entanglement. Upon thermal relaxation, the intermixed amalgam results in "protein entanglement" as re-crosslinking or renaturation occurs to thereby cause a uniform fused-together mass.

DETAILED DESCRIPTION OF THE INVENTION

Various embodiments of the invention provide systems and methods to deliver energy to targeted tissue volumes in a controlled manner to thermally weld or seal targeted tissue. Specific embodiments provide a system including an electrosurgical jaw structure configured to contemporaneously (i) engage tissue between paired jaws, (ii) deliver energy to the tissue, and (iii) optionally, transect the tissue to provide a "one-step" welding-transecting procedure. Embodiments of the invention also provide an electrosurgical jaw structure that can engage and weld tissue bundles, defined herein as bundles of disparate tissue types (e.g., fat, blood vessels, fascia, etc.). For the welding of tissue bundles, the jaw surfaces can apply different energy levels to each different tissue type simultaneously. Related embodiments provide an electrosurgical system that can apply different energy levels across the jaws engagement surfaces using "smart" materials without the need for complex feedback circuitry coupled to thermocouples or other sensors in the jaw structure.

It has been found that very high compression of engaged tissue in combination with controlled Rf energy delivery is desirable for welding the engaged tissue volume. Additionally, it has been found that ohmic heating and dehydration of tissue in the process of closing the jaw structure greatly assists in the ultimate compression of tissue (particularly tissue bundles) to the desired thickness of a membrane. With the engaged tissue in membrane thickness in a controlled gap between the engagement surfaces of the jaw structure, e.g., from about 0.001" to about 0.05", the method for controlling ohmic heating in tissue can be optimized (as described below).

Figure 1:
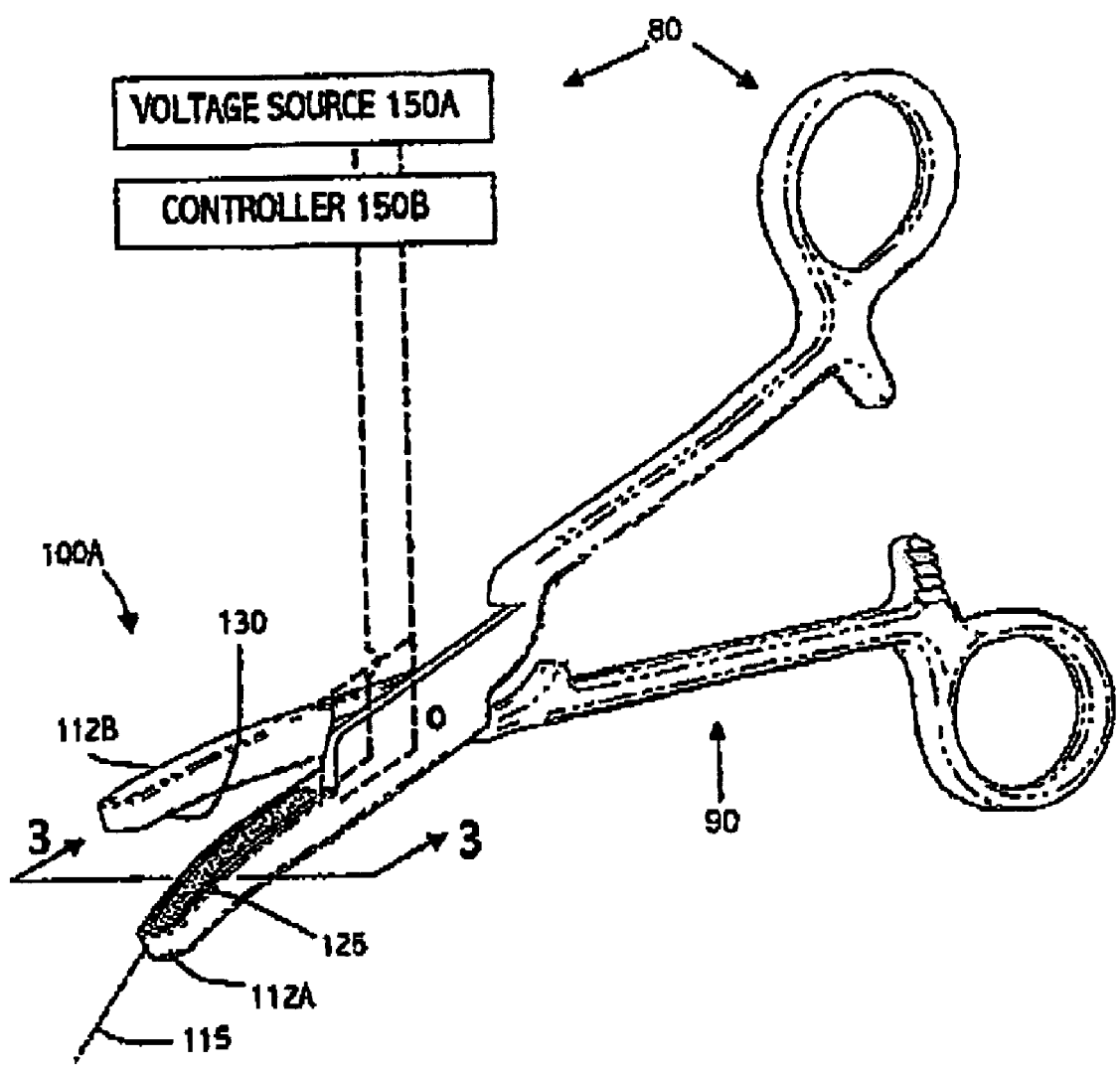
FIG. 1 is a perspective view of an exemplary surgical instrument with and a jaw structure carrying variable resistance matrix bodies for tissue welding corresponding to the invention, the matrix bodies coupled to an Rf source via series and parallel circuits for modulating ohmic heating in engaged tissue.
Figure 3:
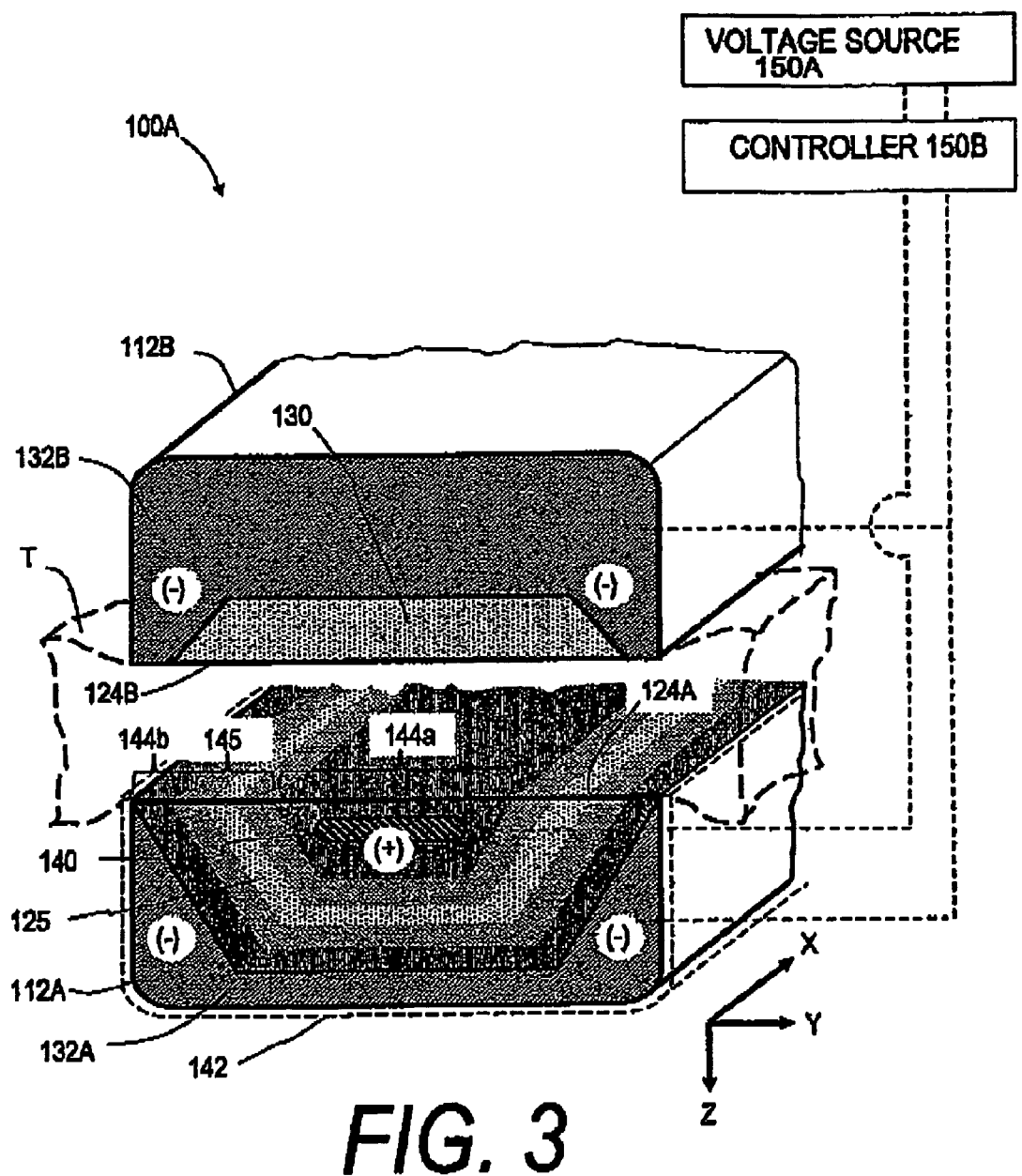
FIG. 3 is a schematic sectional view of the jaw structure of FIG. 1 taken along line 3-3 of FIG. 1 showing the variable impedance matrices in each jaw together with the series and parallel circuits.

FIG. 1 illustrates an embodiment of a system 80 for the application of energy to tissue energy to thermally weld or seal targeted tissue. The system can comprise a surgical instrument 90, a voltage source 150A and controller 150B. Instrument 90 can be a forcep-type instrument as shown in the figure, as well any number of surgical instruments known in the art, including e.g., a scissors, clamps and various minimally invasive surgical instruments known in the art. Surgical instrument 90 includes a working end or electrosurgical jaw structure 100A. Jaw structure 100A is coupled to voltage source 150A and controller 150B for controlling one or more energy delivery parameters, such as the duration of energy delivery (FIG. 3). In preferred embodiments, voltage source 150A is an Rf generator known in the art and the energy delivery parameters are one or more Rf parameters (e.g., power, frequency, duty cycle, total delivered energy, etc.). In these and related embodiments, system 80 is an electrosurgical system for delivering energy to tissue.

In most embodiments, jaw structure 100A comprises first (lower) jaw element 112A and second (upper) jaw element 112B that close or approximate about axis 115 that is straight or curved. Also, the jaw elements can be of any curved or straight shape suitable for open and/or endoscopic surgeries with a scissors-type actions or with one or more cam mechanisms as is known in the art. The jaws also can carry a sliding cutting blade as will be described below.

Figure 2:
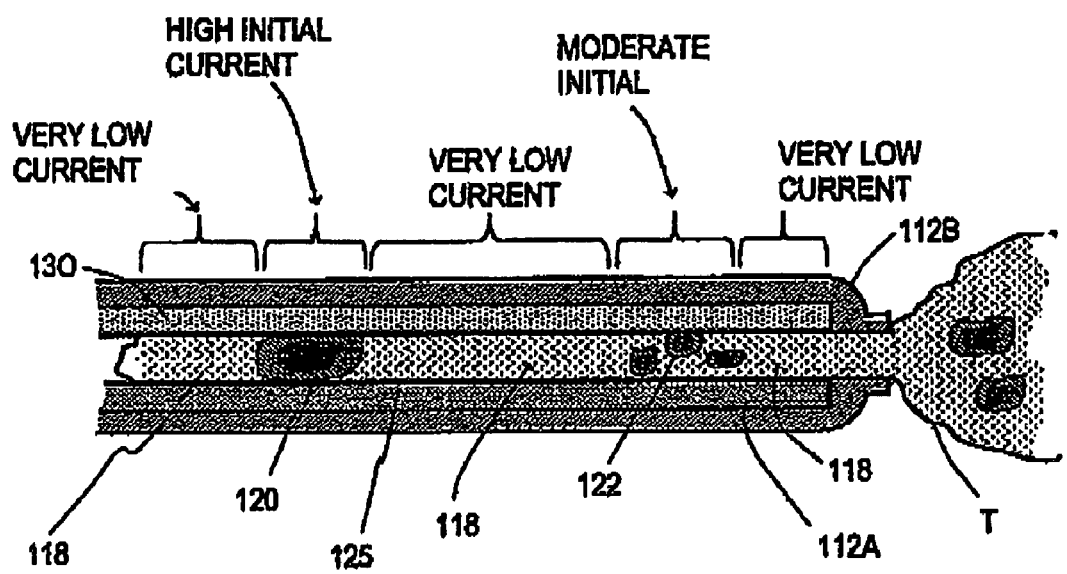
FIG. 2 is a graphic representation of opposing jaws engaging a tissue bundle comprising large blood vessels, fatty tissue and small blood vessels embedded in the fat.

Referring now to FIG. 2, a discussion of the electrosurgical functionality of embodiments of system 80 will now be presented. In FIG. 2, the opposing jaws 112A and 112B are depicted schematically as engaging a tissue bundle T of differentiated tissue types—which is a common occurrence in open and endoscopic surgeries. FIG. 2 depicts a longitudinal sectional view of jaws 112A and 112B and an engaged tissue bundle T that contains, for example, insulative fat 118, large blood vessels 120 and smaller embedded blood vessels 122. The gap between the jaws is not-to-scale, and in an actual jaw structure, the compressed tissue bundle T could be reduced to the thickness of a thin membrane. In an actual procedure, the tissue bundle would likely also contain one or more of fascia, ligamentous tissues and other tissues that could exhibit a wide range of hydration levels, electrolyte levels etc. which in turn, could locally alter tissue impedance, compressibility etc. For convenience, only three tissue types with three impedance levels are shown in FIG. 2; however this figure is only exemplary, and the jaws can be used to engage any number of tissue types (e.g., dermal, muscle, cartilage, etc.) having a variety of physical properties (e.g. hydration, electrolyte concentrations, etc.). As indicated graphically by the micro-currents MC in FIG. 2, embodiments of the electrosurgical jaw structures of system 80 can be configured to contemporaneously modulate energy densities/energy delivery across the various tissue types in the bundle T according to the impedance of one or more of the engaged tissue types and/or engaged regions within the bundle. Further, embodiments of the jaw structures can be configured to continuously modulate energy densities/energy delivery to each tissue type as the engaged tissue types or regions dynamnically changes in hydration, impedance, conductivity and/or geometry. As energy is delivered, the tissue will shrink as it dehydrates.

FIG. 3 illustrates the tissue-engaging surfaces 124A and 124B of jaws 112A and 112B. In various embodiments, the jaws can each include or be coupled to a three-dimensional (3D) temperature-responsive variable resistance body. In many embodiments, the 3D temperature responsive variable resistance body can be carried by the jaws. The lower jaw 112A carries variable impedance body indicated at 125, also at times referred to herein as a positive temperature coefficient of resistance (PTC) body or matrix. The term resistance refers to the electrical resistance of the body or matrix when its is subjected to a DC current. The body or matrix also has an impedance when subject to an alternating current, such as Rf current, as is used in various embodiments of invention. In either case, the resistance or impedance of the body or matrix varies as a function of its temperature. For ease of discussion, the temperature varying electrical properties of the PTC materials/bodies described herein will be described in terms of the material's resistance as a function of temperature; however, the material will also have an impedance that varies with temperature in AC current scenarios. Thus while the PTC bodies described herein are referred to as variable resistance bodies, they also act as variable impedance bodies in AC current scenarios such as Rf current as is used in various embodiments of invention. Also, by the term three-dimensional, it is meant for example, that variable impedance body 125 defines an axial dimension X and a cross-axial dimension Y about the tissue-engaging surface, as well as defining a substantial depth dimension Z that is orthogonal to the plane of the tissue-engaging surface 124A. In other words, the variable resistance body or matrix 125 has a selected thickness dimension in various embodiments to provide a multiplicity of varied local current flow paths through the matrix as it dynamically responds to adjacent ohmically heated tissue, as is discussed herein. The upper jaw 112B in one embodiment shown in FIG. 3 carries variable impedance body 130 that again can have any suitable depth dimension. Further description of PTC materials (including polymer PTC compositions), their properties and methods of manufacture may be found in concurrently filed application Ser. No. 10/993, 210 which is fully incorporated by reference herein.

Still referring to FIG. 3, it can be seen that lower jaw 112A can have a structural component or body 132A that is of a suitable electrical conductor material so that it functions as an electrode—that is indicated for convenience with a negative polarity (−). Similarly, the upper jaw 112B has structural component or body 132B that is has the same polarity (−) as the lower jaw body. An electrically conductive member or electrode 140 is provided within variable impedance matrix 125 either at the tissue-engaging surface 124A or proximate the surface as depicted in FIG. 3. Both jaws optionally can have an insulative coating indicated at 142 at the exterior of lower jaw 112A. Coating 142 can positioned over all or portion of jaw 112A.

In a preferred embodiment shown in FIGS. 2 and 3, the variable impedance matrices 125 and 130 in lower jaw 112A and upper jaw 112B comprise a polyethylene or a medical grade silicone polymer that is doped with conductive particles (e.g., carbon) using doping methods known in the art. The use of such temperature-responsive variable impedance materials is described for related uses in co-pending U.S. patent application Ser. No. 10/351,449 filed Jan. 22, 2003 entitled Electrosurgical Instrument and Method of Use; Ser. No. 10/032,867 filed Oct. 22, 2001 entitled Electrosurgical Jaw Structure for Controlled Energy Delivery, and in Ser. No. 10/933,210, entitled Polymers Compositions Exhibiting Highly Nonlinear PTC Effects And Methods Of Fabrication all of which are incorporated herein by reference. Polymer positive temperature coefficient materials are known in the field of overcurrent protection devices that will trip and become resistive when a selected trip current and temperature are exceeded.

Figure 4A:
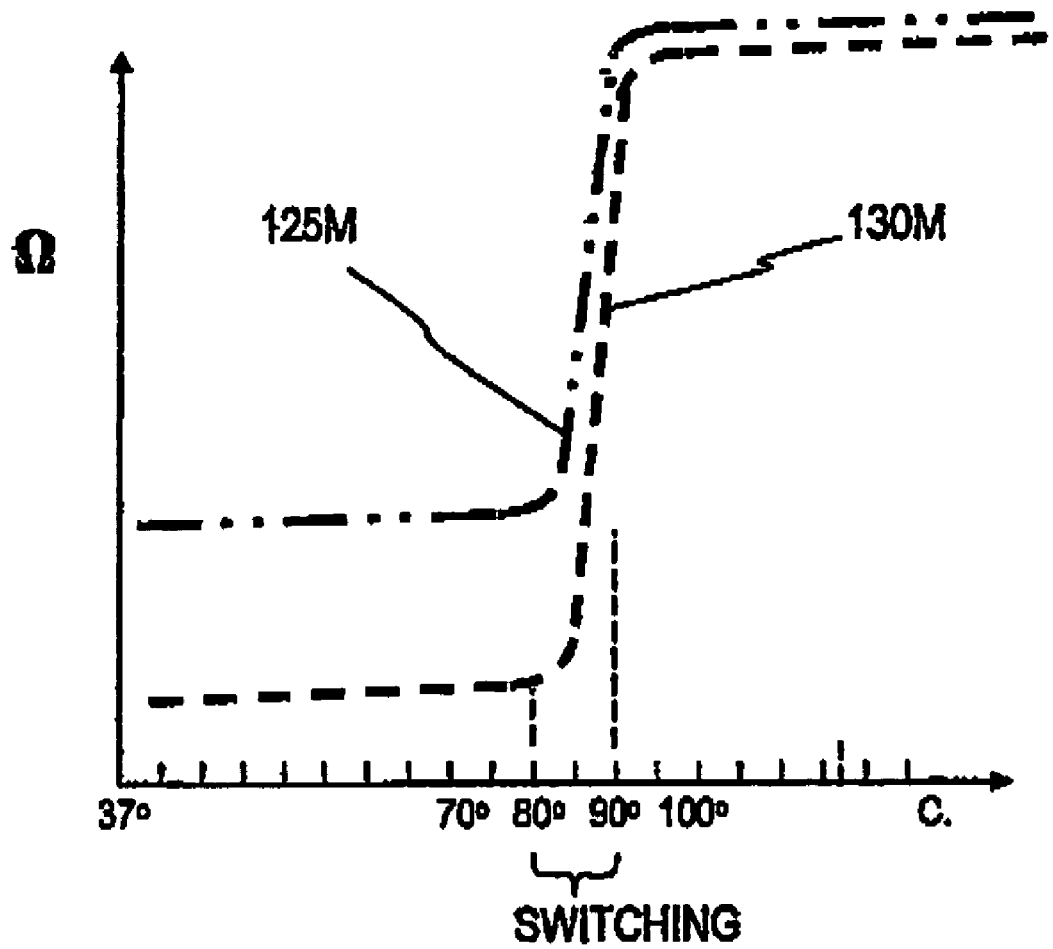
FIG. 4A is a diagram of the temperature-resistance curves of exemplary variable resistance matrix bodies as in FIG. 3.

Various embodiments of the temperature-responsive variable resistance materials described herein can be fabricated from a non-conductive polymer that exhibits two phases and geometries that define greater and lesser conductive states. The first phase is a crystalline or semi-crystalline state where the polymer molecules form long chains and are arranged in a more ordered architecture. When the temperature of the material is elevated, the polymer molecules maintain the crystalline architecture or structure—but eventually transition to an at least partly amorphous phase from the crystalline state. In the amorphous state, the molecules are aligned more randomly, and there may be a slight change in actual material geometry. The non-conductive polymer is combined with a dispersed, highly conductive particles, e.g., carbon nanoparticles to form a matrix. In the crystalline phase of the polymer, the carbon particles are packed into the crystalline boundaries and form many conductive paths across and through the matrix material. In this low temperature crystalline state, the polymer-carbon matrix is engineered to have a low resistance. FIG. 4A illustrates the positively-sloped resistance-temperature curve 130M of an exemplary variable resistance matrix 130 of FIG. 3. Note that the curves in FIGS. 4A and 4B can also be expressed in terms of resistivity (which accounts for effects from the length and/or thickness of the material as is known in the art) and will generally have the same shape.

In an embodiment of a method of the invention using an electrosurgical jaw structure, jaw structure 100A of FIG. 3 is used to engage tissue and apply Rf energy to the engaged tissue T to cause ohmic heating therein. After the tissue is elevated in temperature, heat is conducted from the engaged tissue T back to the variable resistance matrices 125 and 130 to thereby elevate temperatures in at least surfaces region of the matrices 125 and 130. Details of the actual method of using the matrices to provide high temperature and low temperature process limits are described below. As long as the temperature increase in the matrix portion adjacent the ohmically heated tissue does not cause a phase change in the polymer, current can flow unimpeded through the matrix. When the temperature of the matrix material is elevated to a selected temperature, called a switching range herein, the temperature will cause a phase change in the polymer (see FIG. 4A). The crystalline structure of the polymer will disappear, the polymer volume may expand slightly and the carbon chains that allow for conduction across the matrix will be broken—an extraordinary increase in resistance. The polymer-carbon matrix can define a resistance measured in milliohms or ohms before the phase change. After the phase change, the matrix' resistance can be measured in megaohms. Current flow can be reduced accordingly or terminated. In this way, embodiments using variable resistance matrices can be used to precisely control energy densities in the engaged tissue. Such control in turn allows for one or more of the following: 1) more uniform heating and/or temperature distribution of the engaged tissue; 2) a more uniform thermal affect in the engaged tissue; 3) more uniform welds in the engaged tissue; 4) more precise control of energy delivery parameters (e.g., rate and total energy delivered); 5) reduced and incidence of tissue charring and/or desiccation; and 6) reduced thermal injury/effect to non-target tissue.

The process described above is reversible so that when a portion of a matrix falls in temperature, the polymer component will return to its crystalline structure and the matrix volume will return to its original state. The conductive carbon particles will reform into conductive paths within the interstices of the crystalline polymer architecture. The exact same conductive paths appear not to reform themselves after first use of the matrix, and for this reason the polymer matrices of the invention may be temperature cycled several times in the fabrication process which appears to cause the material to have substantially resettable conductive paths. In the fabrication process, the matrix can also be treated in various processes (e.g., gamma, UV irradiation etc.) to cross-link the polymer or co-polymers of the matrix.

Figure 4B:
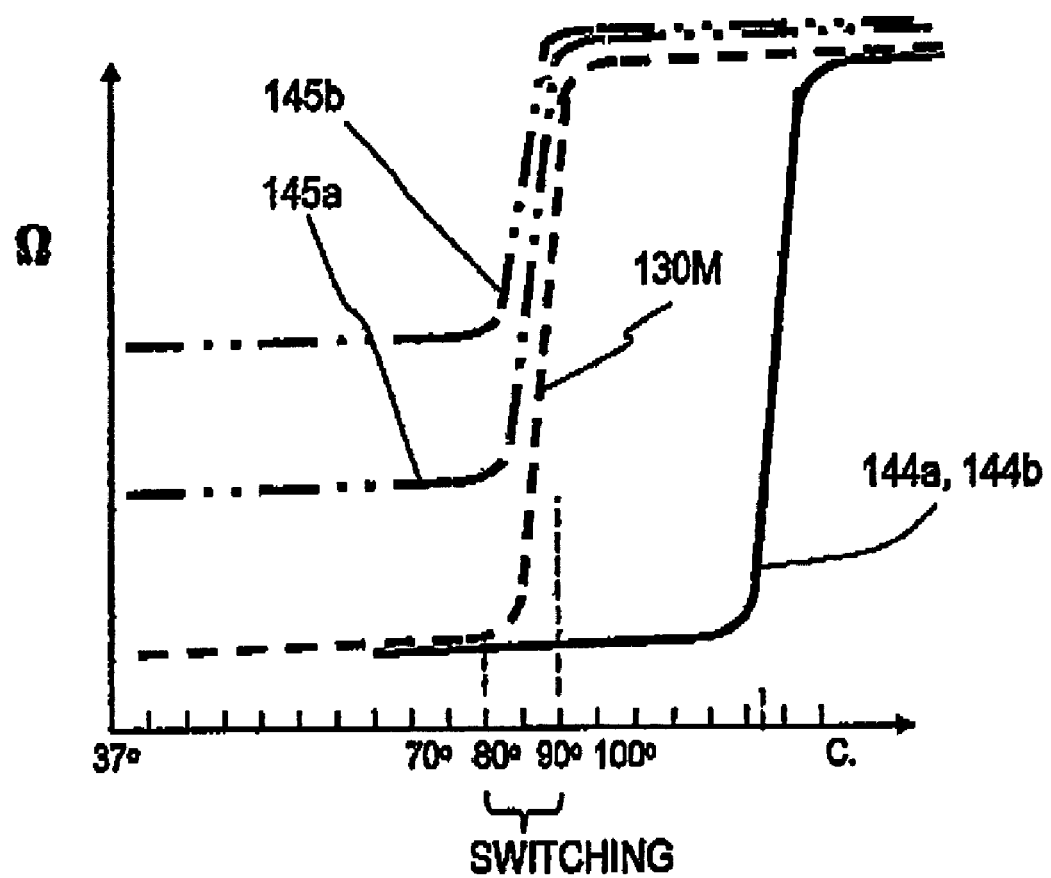
FIG. 4B is a diagram similar to that of FIG. 4A illustrating alternative temperature-resistance curves of variable impedance matrix bodies.

Referring again to FIG. 3, various embodiments of polymer matrix 125 can comprise at least two differentiated regions 144 and 145 that have different temperature impedance responses so as to have different temperature-impedance curves as illustrated in FIG. 4B. The regions 144a and 144b (collectively 144) at the center of the lower jaw and the laterally-outward edge of the jaw are comprised of a highly conductive matrix that will only terminate current flow therethrough at a high temperature, for example between 100° C. and 200° C. as shown in FIG. 4B. These regions 144, effectively function as the opposing polarity conductive electrodes as the regions 144 are in contact with the central first polarity conductor 140 and the second polarity jaw body 132A. The lower jaw's matrix region 145 can be configured to provide a plurality of slightly different regions 145a and 145b that have somewhat different base resistances and/or switching ranges as shown in FIG. 4B for reasons described below. Further, one or both of regions 144 and 145 of matrix 135 can be positioned intermediate opposing polarity conductor portions 140 and 132A.

In various embodiments, matrices 130 and 140 can have impedance characteristics chosen so as to yield a selectable relationship between the impedance characteristics of the two matrices. Such impedance characteristics can include without limitation, baseline impedance and temperature impedance response including one or more of the slope, shape and switching range of the temperature impedance response curve. For example, in one embodiment, the matrix 130 can be have a higher or lower base resistance and/or a steeper or flatter response curve vs. matrix 140. In one embodiment, matrix region 145 can have a base resistance that is somewhat higher than that of matrix 130 in the upper jaw 112B. Further the relationship between impedance characteristics of matrices 130 and 140 can be configured to enhance the ability of the matrices to modulate the delivery of energy to tissue, including the ability of the matrices to modulate or control one or more of tissue current density, tissue temperature and peak tissue temperature.

Figure 5:
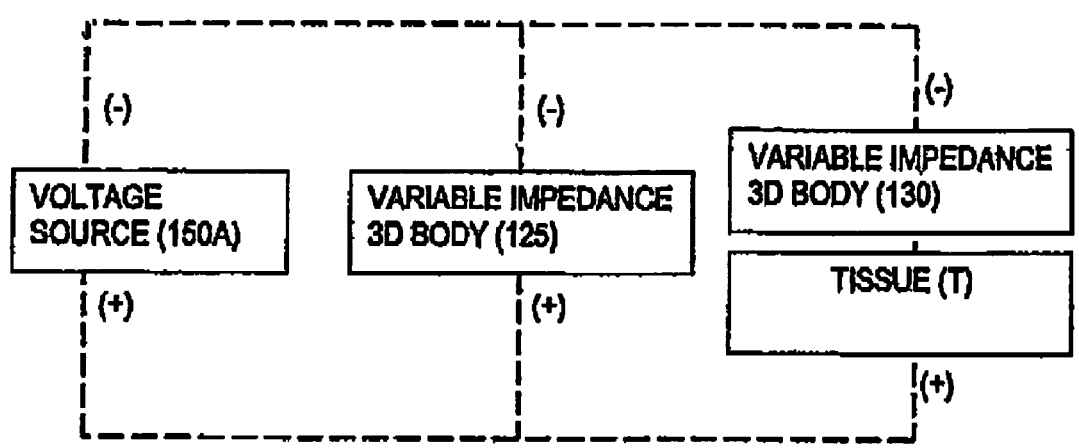
FIG. 5 is a block diagram of the series and parallel electrical circuit components of the working end of FIG. 3.

A discussion will now be presented of the manner in which matrices 125 and 130 can operate to modulate energy delivery in tissue. In various embodiments, the jaw structure 100A can be configured to utilize the two differently performing matrices 125 and 130 (e.g., as illustrated in FIG. 3) in combination with the series and parallel circuitry of FIG. 5 to provide effective high and low process limits for temperatures and energy densities in the engaged tissue T. It has been found that such dynamic energy and temperature controls are desirable for creating uniform thermal effects in tissue to denature tissue proteins and to create high strength welds. In one embodiment as in FIG. 3, the matrix 130 in upper jaw 112B is configured to exhibit unique temperature-impedance characteristics represented by the positively-sloped curve 130M of FIG. 4B. This matrix 130 maintains a relatively low base resistance over a selected base temperature range with a dramatically increases resistance above a selected narrow temperature range (switching range) that can be any 1° to 10° range between about 50° C. and 200° C., and more preferably between about 70° C. and 120° C. In comparison, the matrix region 145 in lower jaw 112A is designed to have an impedance-resistance curve exhibiting a higher initial base resistance (see FIG. 4B). The matrix region 145 provides this higher base resistance over a similar temperature range as matrix 130. The matrix 145 and its temperature-impedance curves (145a, 145b) in FIG. 4B again exhibits a dramatically increasing resistance above its selected switching range, which can fall in the range described previously with reference to matrix 130.

Figure 6:
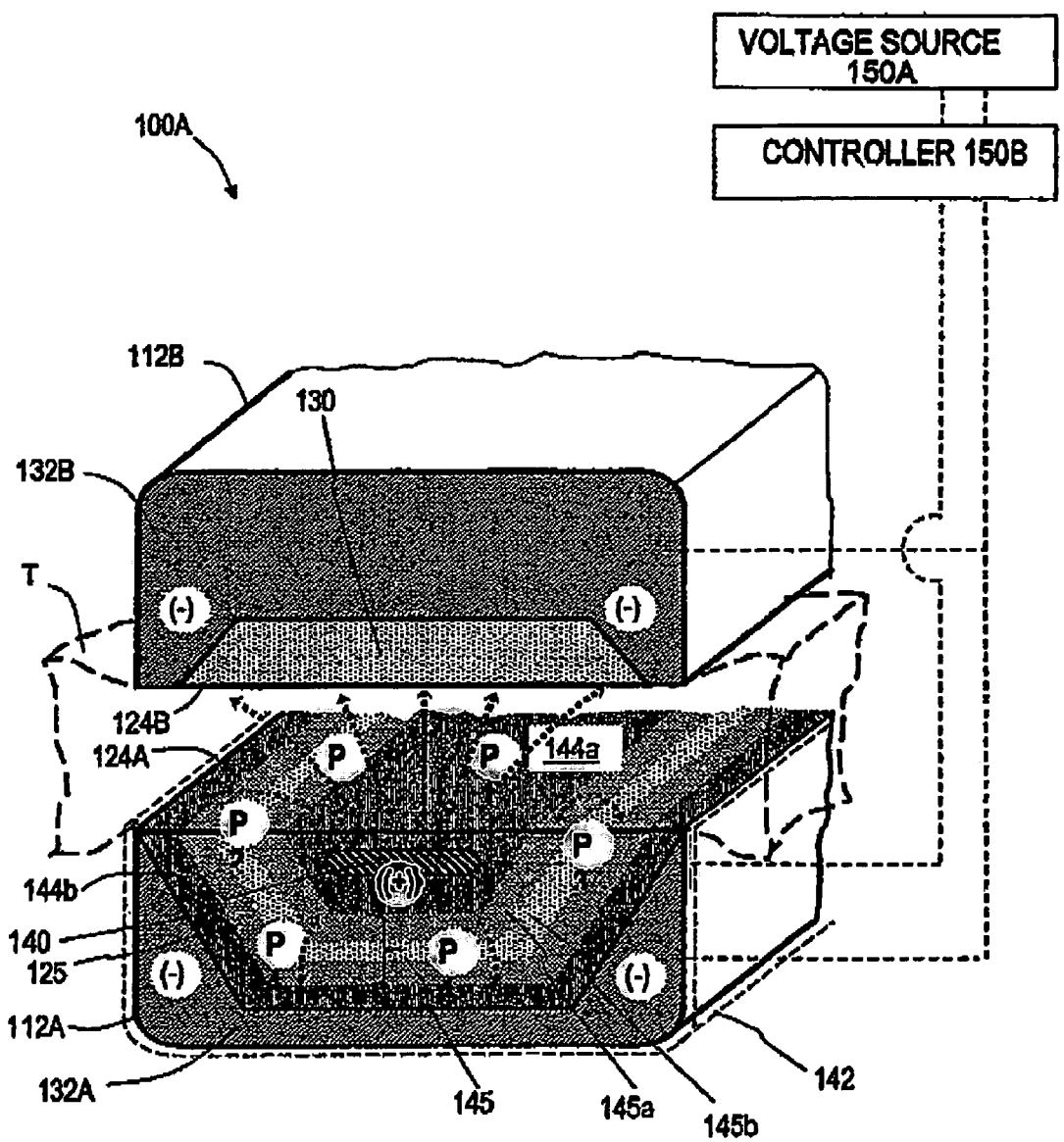
FIG. 6 is a sectional schematic view of the variable impedance matrix bodies showing potential current flow paths in the engaged tissue and the matrix bodies.

Referring now to FIG. 6, a discussion will be presented of the self-modulating properties of various embodiments of jaw structure 100A. FIG. 6 graphically depicts the manner in which the jaw structure 100A of FIGS. 1 and 3 can self-modulate current flow among multiple paths—depending on the temperature of the engaged tissue and other electrical conduction parameters of the tissue to which the matrices 125 and 130 respond. FIG. 6 again depicts a sectional view of the jaws 112A and 112B as in FIG. 3 engaging tissue T in phantom view. In FIG. 6, the tissue thickness is not to scale to allow a graphic representation of potential current paths. In use, the working end 100A of FIG. 6 can be configured to have the ability to modulate current flow among multiple different paths through the tissue T as well as through the matrices 125 and 130. Current and voltage in the tissue T is modulated after the tissue is ohmically heated—and thereafter heat from the tissue T is transferred by passive conduction to adjacent regions of matrices 125 and 130. While there will exist a multiplicity of potential current paths in the engaged tissue and matrices, FIG. 6 illustrates four different flow paths, P1 through P4, that provide a means for a self-modulating energy control system used by various embodiments of the invention. These paths are exemplary, and other paths not shown are equally applicable. Energy levels in each flow path are dynamic during Rf energy delivery to tissue, which will be described in more detail below. In FIG. 6, flow paths P1 indicates potential Rf microcurrent flows directly through tissue T between first polarity electrode 140 and conductive region 145 and the low resistance matrix 130 of upper jaw 112B that overlies the (opposing) second polarity jaw body 132B. It can be understood that these current paths P1 provide initial rapid ohmic heating of tissue. Flow paths P2 indicate Rf current flow through tissue T between the highly conductive regions 144a and 144b that are laterally spaced apart in the lower jaw that are in contact with first polarity conductor 140 and second polarity jaw body 132A, respectively.

In various embodiments, working end 100A can be configured to use potential current flow paths indicated at P3 and P4, to modulate ohmic heating in engaged tissue as its conductive parameters (e.g., impedance, temperature, hydration, etc.) are dynamic during energy application. Potential flow paths P3 represent potential microcurrent paths through a region of tissue between spaced apart surface portions of matrix 125 that engage such a tissue region. Potential current flow paths P4 are at an interior of the jaw and the 3D matrix 125 wherein current can flow generally from electrode 140 across the matrix region 145 to the interior of the opposing polarity jaw body 132A. A more detailed step-by-step description of current flow modulation is provided below in the text accompanying FIGS. 10A-10D.

For clarity of explanation, FIG. 6 depicts the principles of the working end in a basic forceps-type jaw structure 100A of FIGS. 1 and 3. However it should be appreciated that matrices 125 and 135 can be configured to be used in any number of surgical instruments known in the art. For example, the same variable resistance matrices 125 and 130 can be provided in embodiments of a jaw structure indicated at 100B in FIGS. 7 and 8 that carry a blade or other cutting means for transecting the welded tissue. Further, the same variable impedance matrices 125 and 130 can be carried in a one-step jaw structure that is described below (see FIGS. 11-12) wherein jaw closing, Rf energy delivery and tissue transection occur in a single operation.

Figure 7:
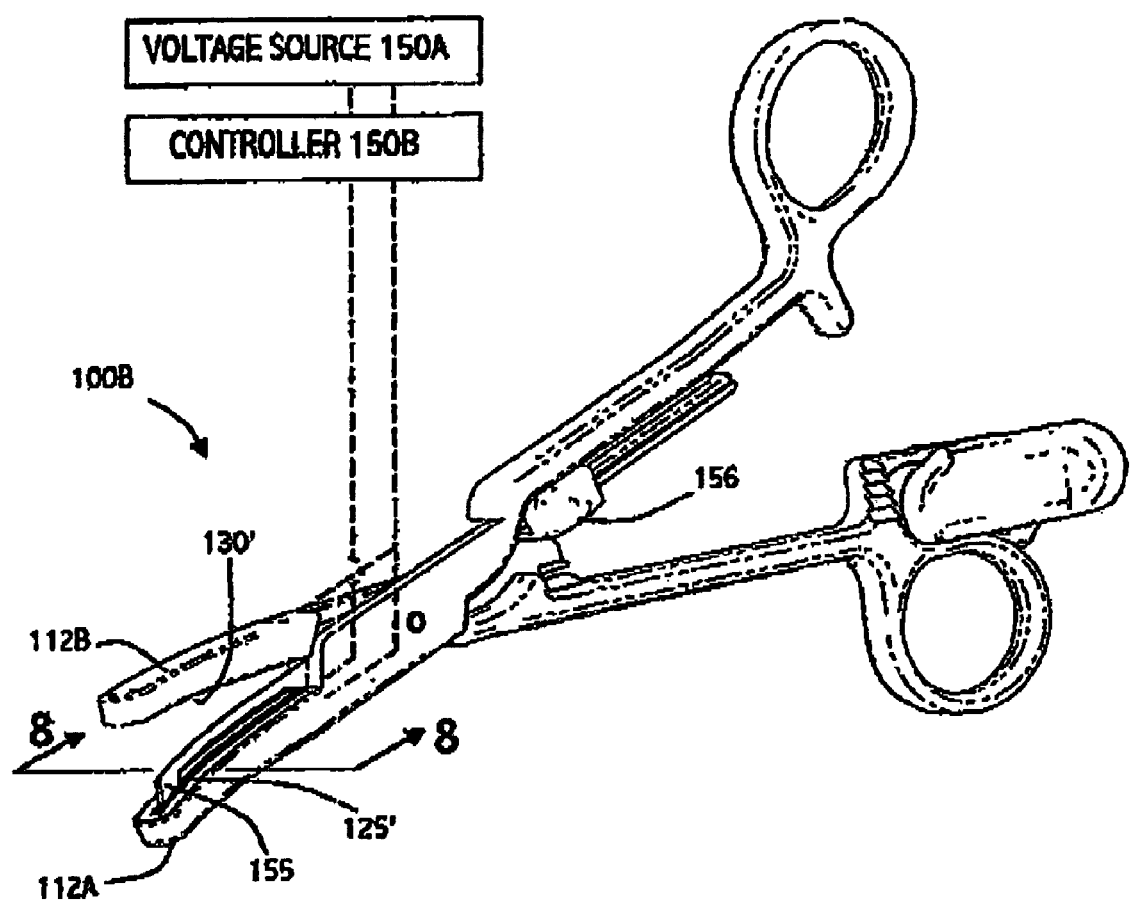
FIG. 7 is a perspective view of an alternative instrument with and a jaw structure carrying variable impedance matrix bodies together with blade means for transecting tissue.
Figure 8:
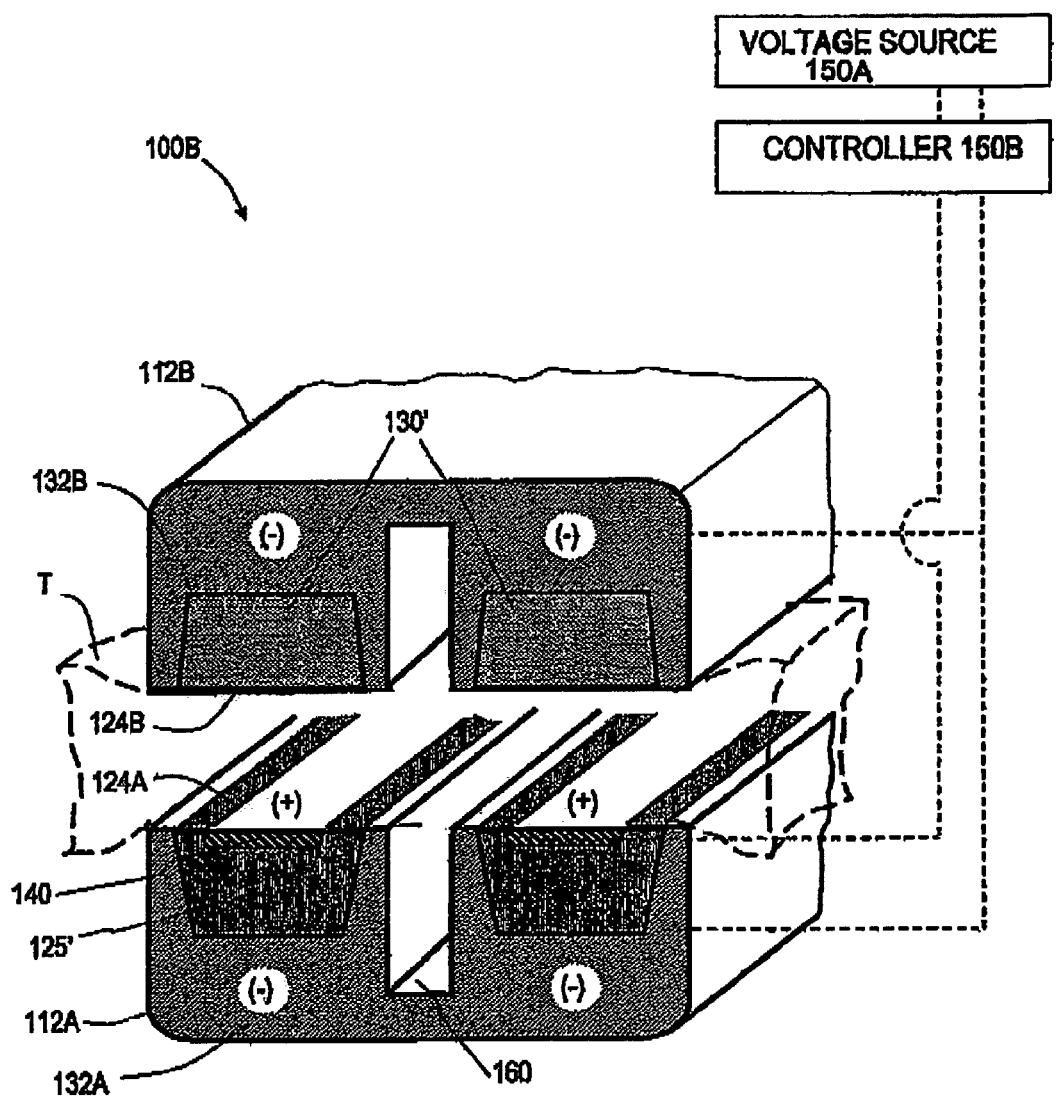
FIG. 8 is a sectional view of the jaw structure of FIG. 7 taken along line 8-8 of FIG. 7 showing the variable impedance matrices in each jaw together blade means.

Referring now referring to FIGS. 7 and 8, a forceps-type instrument is shown with a detachable cartridge 154 that carries a thin flexible blade member 155 that can be pushed by thumb slider 156 when the jaws are locked in a closed position. Such a blade cartridge was disclosed in co-pending U.S. patent application Ser. No. 10/443,974, filed May 22, 2003 entitled Electrosurgical Working End with Replaceable Cartridges which is incorporated herein by this reference.

FIG. 8 illustrates a cross section of the upper and lower jaws 112A and 112B with a central blade slot 160 for receiving the slidable, flexible blade member 155. On either side of the blade slot 160, the jaw bodies carry variable resistance matrices 125' and 130' that are similar (or identical) to the matrices depicted in FIG. 3. In the exemplary embodiment of FIG. 8, the lower jaw 112B has a matrix 125' that is simplified in that electrode 140 is exposed in the center of the jaw's engagement surface 124A with a portion of the 3D matrix 125' extending laterally on either side of blade slot 160 as well as within the interior of the jaw. As can be seen in FIG. 7, matrix extends in a "U"-shape around the end of blade slot 160 to allow welding of engaged tissue around the end of a welded and transected tissue region. In various embodiment blade member 155 can comprise other surgical cutting means known in the art.

Figure 9:
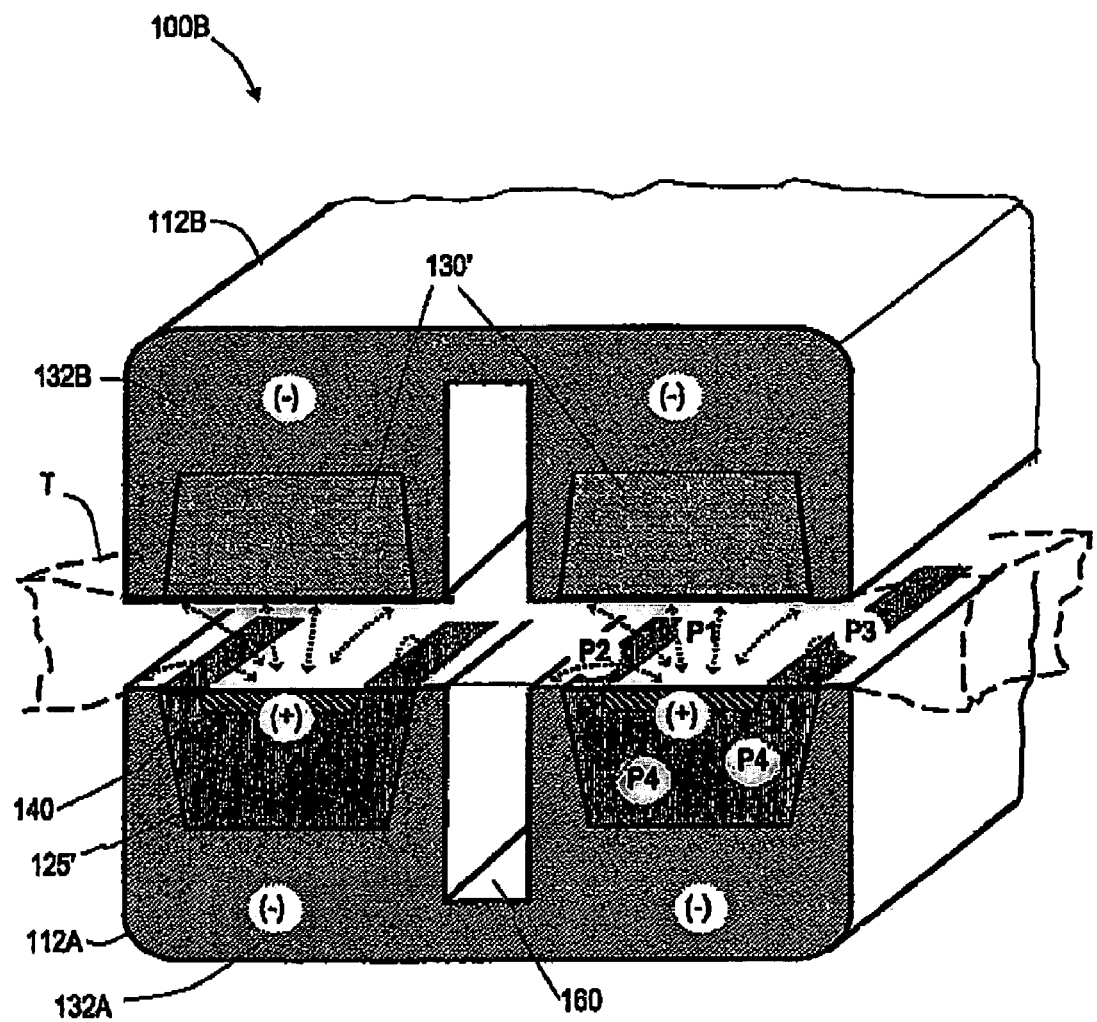
FIG. 9 is a sectional schematic view of the jaw structure of FIGS. 7-8 that illustrates potential current flow paths in the engaged tissue and the matrix bodies.

In various embodiments, the working end 100B of FIGS. 7-8 functions to modulate Rf energy application to tissue in between multiple potential paths as described above and depicted in FIG. 6. FIG. 9 illustrates the working end 100B of FIGS. 7-8 and again graphically depicts the potential Rf current paths in tissue and across regions of the variable resistance matrices. The current paths P1, P2 and P3 again represent potential paths in the engaged tissue T. In FIG. 9, the current paths P4 represent paths within the interior regions of matrix 125' between first polarity (+) surface conductor 140 and a second polarity (−) region of jaw body 132A.

Referring now to FIGS. 10A-10D, a discussion will now be presented of various methods of utilizing temperature responsive variable resistance matrices for Rf modulation in tissue welding and other electrosurgical applications (e.g., cut, coagulation, etc.) FIGS. 10A-10D graphically illustrate the sequential energy delivery phases in a method of the invention. In FIGS. 10A-10D, the opposing jaws 112A and 112B are depicted engaging a tissue bundle T, and Rf energy application to tissue is modulated by matrices 125 and 130 between various paths P1-P4 in the tissue to create a uniform temperature without desiccation or charring to provide an effective high strength weld. FIGS. 10A-10D illustrate a basic jaw structure 100C similar to that of FIG. 1 without a blade member, but it should be appreciated that a jaw 100B with a reciprocal blade as in FIGS. 7-8 would create a weld by the same means of energy application and modulation. For clarity of explanation, the engagement surface 124A of FIGS. 10A-10D has the central conductive member or electrode 140 exposed in the surface (cf. FIGS. 7-9).

Figure 10A:
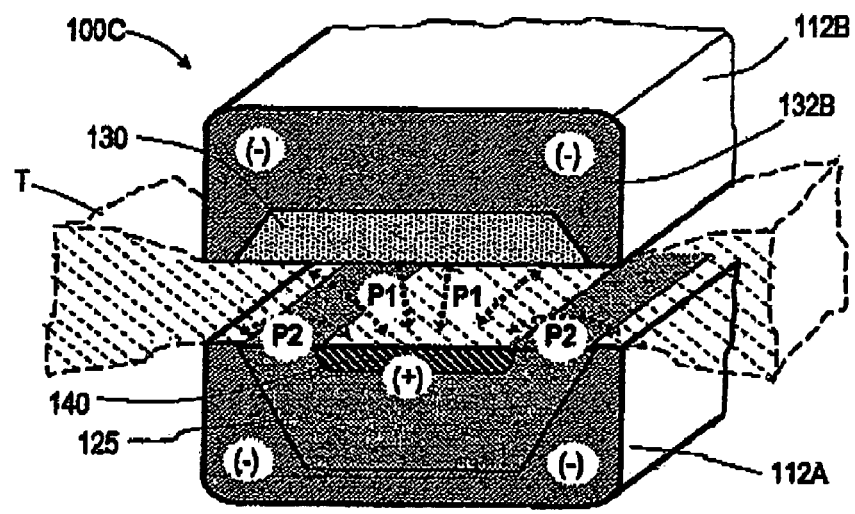
FIG. 10A is a sectional view of the jaw structure of FIGS. 7-8 illustrating an initial step in a method of the invention wherein Rf current flow paths cross the engaged tissue to cause ohmic heating therein.

Now turning to FIG. 10A, an initial energy application step is illustrated wherein tissue bundle T is engaged as the jaws apply compression and the surgeon applies Rf energy to the tissue. At initiation of Rf energy application, FIG. 10A illustrates that current flows are substantially through the tissue between the first polarity conductor 140 and the opposing matrix 130 and laterally-outward upper jaw 132B as well to the second polarity lower jaw body 132A, that is in paths P1 and P2 as depicted in FIGS. 3 and 9. Thus, FIG. 10A depicts current flow that causes very high energy densities and very rapid ohmic heating in the engaged tissue T. In this initial phase of Rf energy application to the jaw structure 100C and to the engaged tissue T, the matrices 125 and 130 are, in effect, in a stand-by mode and are not yet operating to modulate flow paths of the microcurrents in the tissue. The matrix 130 in the upper jaw at ambient room temperature has a low base resistance (see FIG. 4B) and allows a multiplicity of conductive flow paths all across and through the matrix 130 to the second polarity jaw body 132B from the first polarity conductor 140 in the lower jaw through the tissue T.

In FIG. 10A, the ohmically heated tissue causes conductive heat transfer to the matrices 125 and 130 to heat at least the surface regions of both matrices. At the same time (see FIG. 10B) the ohmically heated tissue T dehydrates, changes its geometry by shrinking and exhibits an increased impedance. In this phase of energy application, the variable resistance matrix 130 responds according to its selected temperature-resistance curve (see FIG. 4B) wherein the material regulates and modulates flow paths P1 of microcurrents therethrough. For example, the switching range of matrix 130 can be between about 60° C. to 120° C. and is more preferably in the 70° C. to 90° C., range. During and following this phase, the impedance of tissue regions will be substantially matched by the induced impedance of adjacent regions of matrix 130, to thereby modulate current flow in paths P1 between the jaws. In this way, matrix 130 acts as an impedance matching 3D body.

In addition to impedance matching, matrix 130 can also operate to prevent or significantly reduce the possibility of arcs or sparks at the interface of jaw surfaces 124A and 124B with the engaged tissue since, current flow will be eliminated before excessive high temperatures are reached about any region of the tissue-jaw interfaces. The prevention of such arcs eliminates the possibility of unwanted tissue charring. In this way, matrix 130 provides a means for not only preventing or reducing arcing, but also for reducing or preventing tissue charring and/or other unwanted thermal injury to tissue. This in turn, reduces thermal injury or damage to collateral tissue outside the target tissue region.

Figure 10B:
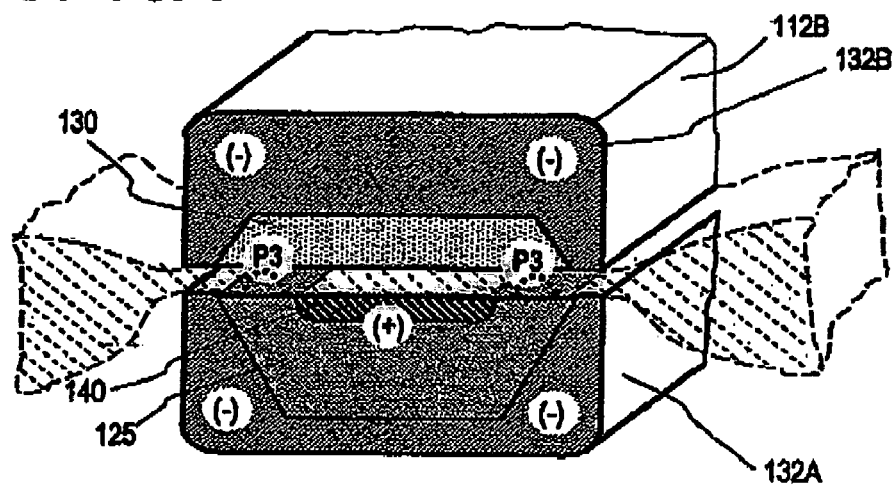
FIG. 10B is a sectional view of the jaw structure of FIG. 10A depicting a subsequent step in a method of the invention with modulated Rf current flow paths in the engaged tissue.

During the initial energy application phase illustrated in FIGS. 10A and 10B, the ohmically heated tissue also will conduct heat back to matrix 125 in the lower jaw 112A to elevate the lower matrix above its selected switching range, for example in the 70° C. to 90° C., range. Still referring to FIG. 10A, as the thickness of tissue T is reduced by compression and ohmic-induced dehydration, the increased impedance of the tissue will first prevent microcurrent flows in paths P1 as the upper jaw's matrix 130 is masked. At this point, there will remain the possibility of microcurrent flows in paths P2 between the electrode 140 and the laterally-outward jaw body portion 132A.

Now referring to FIG. 10B, it can be seen that the dehydrated tissue T typically will be compressed to a thin membrane which can increase its impedance in the most direct paths of current (P1 and P2) between the opposing polarity body portions. With the tissue in this condition, the reduction or termination of ohmic heating will cause slight cooling of the tissue and re-hydration of the tissue can occur due to inward fluid migration. In this state, the lower matrix 125 will respond by cooling and then by causing microcurrent flows in paths P3 as indicated in FIG. 10B. Of particular interest, the increase in ohmic heating is then localized is these lateral regions of the engaged tissue while the tissue impedance still masks the upper jaw matrix 130. During this regulated phase of Rf energy application, the engaged tissue may hydrate to allow current flows in paths P1 and P2 to cause additional ohmic tissue heating. Thus, it can be understood how the temperature responsive matrices will self-modulate ohmic energy densities in the tissue between the various potential flow paths.

Figure 10C:
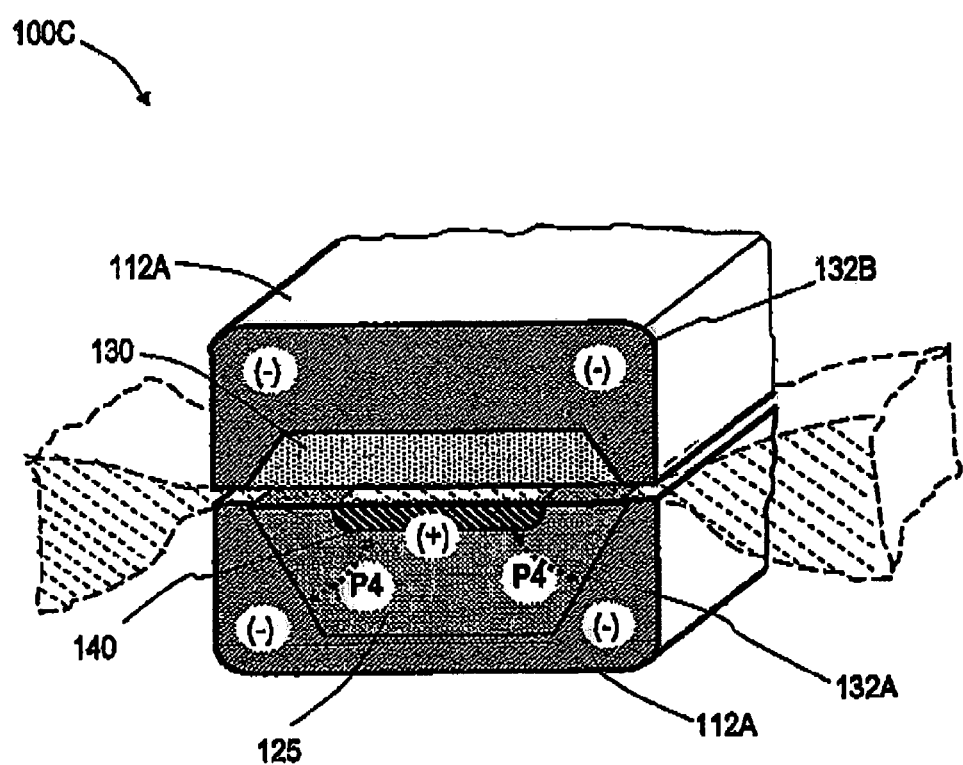
FIG. 10C is another sectional view similar to FIGS. 10A-10B depicting a step in a method of the invention wherein Rf current flow paths within an interior of a variable impedance matrix prevent sparking at a jaw engagement surface.

FIG. 10C indicates another potential flow path P4 that can come into play if any voltage occurs that could cause an arc at the jaw-tissue interface. In effect, the energy can be dissipated by energy flows in the paths indicated at P4 between the first polarity conductor 140 and the second polarity lower jaw body 132A directly through the lower matrix 125 at the jaw's interior.

FIGS. 10A-10C indicate generally how the temperature-responsive matrices 125 and 130, at the tissue-engaging surfaces 124A and 124B, will modulate ohmic heating in the engaged adjacent tissue T. It should be appreciated that the energy modulation also occurs about very localized regions of the engaged tissue T that is made up of different tissue types as discussed in the text accompanying FIG. 2. Thus as any local region of tissue impedance changes during ohmic heating, the local adjacent region of matrix 130 in the initial phase will move to an impedance matching level.

Further, as described above, the tissue dimension and geometry between the engagement surfaces 124A and 125B of the jaws is dynamic and shrinking during ohmic heating of the tissue T. Thus, the local dynamics of ohmic heating in tissue along the axial length of the jaw can be significant.

Figure 10D:
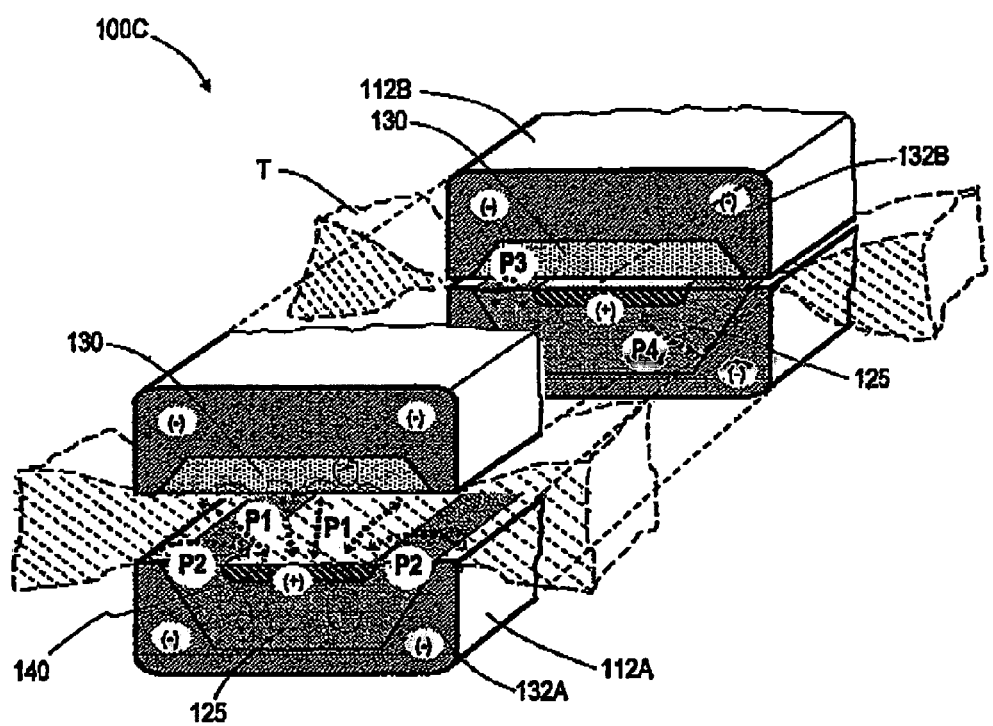
FIG. 10D is another view similar to FIGS. 10A-10C depicting a step in a method of the invention wherein Rf current flow paths occur in different axial regions of the jaws depending on local jaw compression.

FIG. 10D illustrates the pivoting jaw structure 100C as applying higher compression to more proximal tissue regions and the jaws close and the tissue dehydrates and shrinks during energy delivery. It can be understood that ohmic heating is thus modulated by matrices 125 and 130 in the jaws' engagement surfaces to provide locally independent energy densities in discrete tissue regions depending on local tissue temperature and impedance—as well as tissue geometry.

It has been found that the system described above can be operated with a pre-set duration of Rf energy delivery, wherein energy flow and tissue heating is self-regulated by matrices 125 and 130 to effectively provide high and low process limits for the selected duration of energy application. Depending on selected power levels and selected matrix parameters, duration of energy application to create an effective weld can range between about 1 second and 20 seconds, and more preferably is between about 3 second and 15 seconds.

Figure 11:
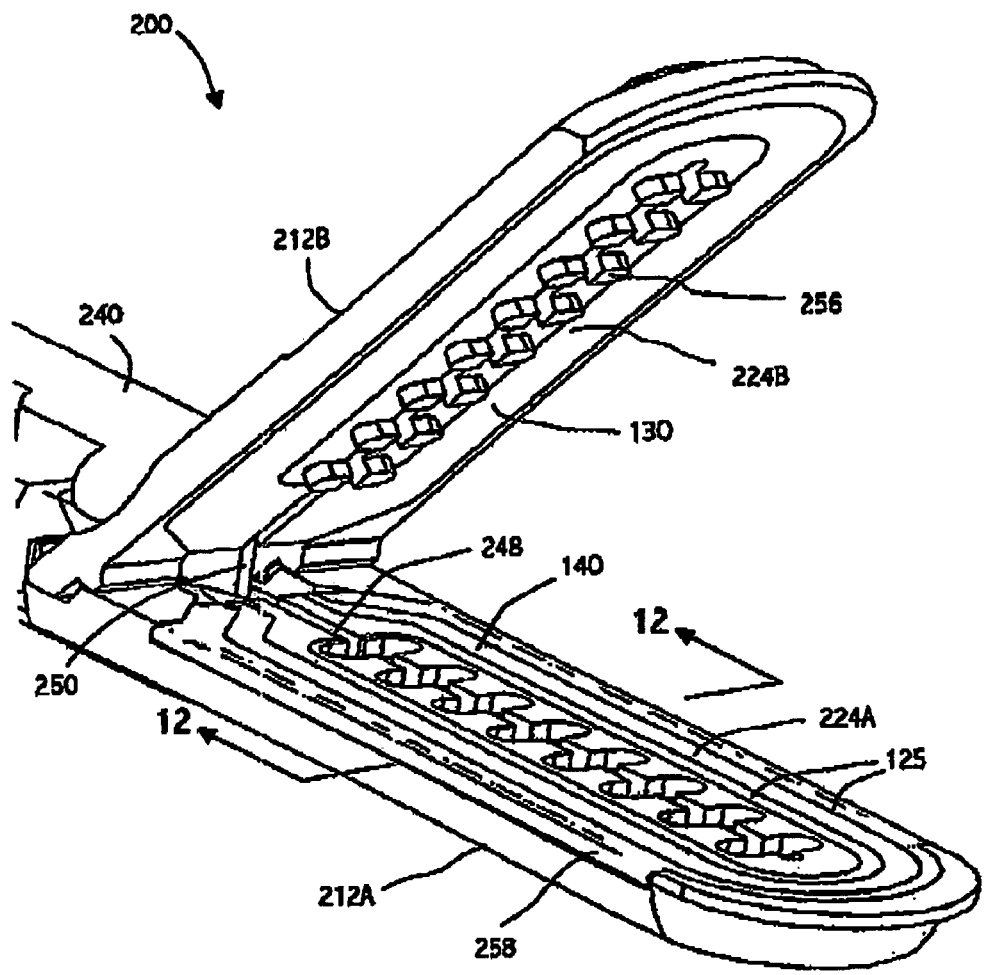
FIG. 11 is a perspective view of an alternative high-compression jaw structure carrying 3D variable impedance matrix bodies that is adapted for one-step tissue welding and transection corresponding to the invention, the matrix bodies coupled to an Rf source via series and parallel circuits.
Figure 12:
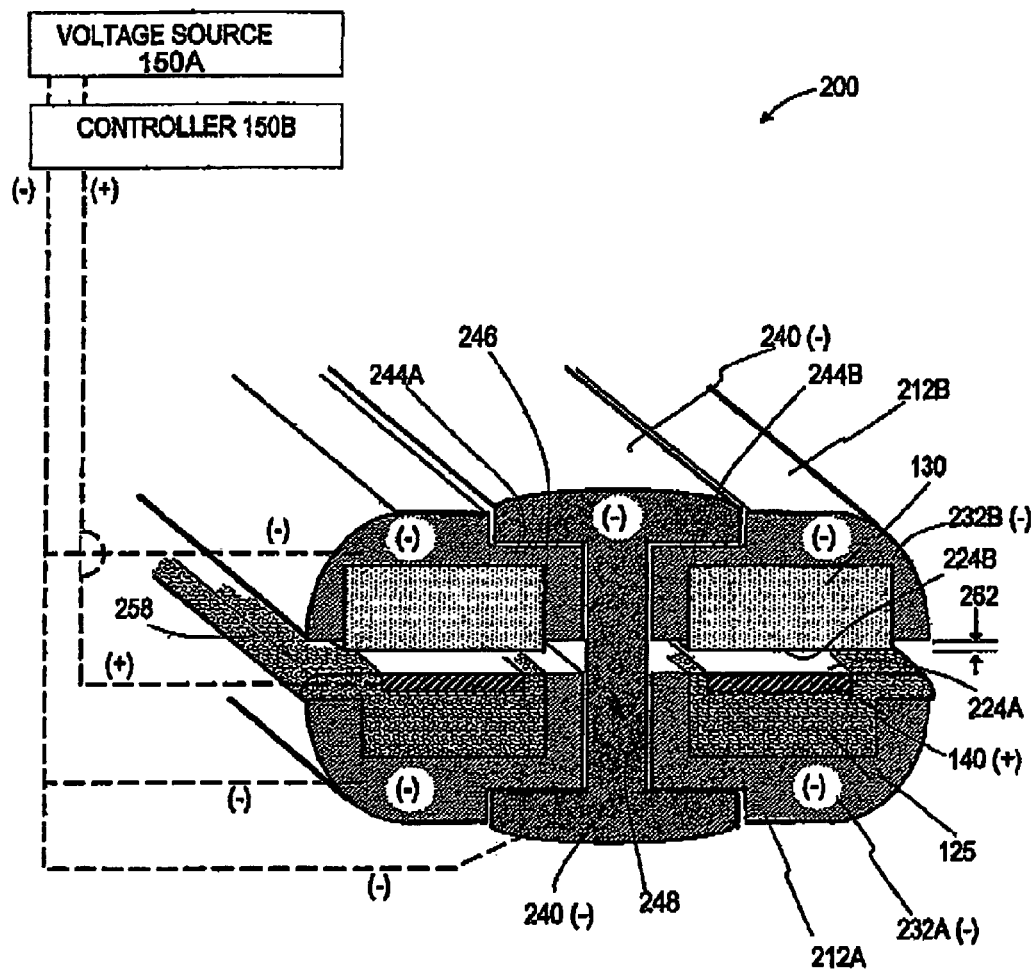
FIG. 12 is a schematic sectional view of the jaw structure of FIG. 11 taken along line 12-12 of FIG. 11 showing the variable impedance matrices in each jaw together with the series and parallel circuits.

Referring now to FIGS. 11 and 12, another embodiment of jaw structure 200 is illustrated that carries cooperating variable resistance matrices as descried above. The upper and lower jaws 212A and 212B have respective engagement surfaces 224A and 224B that carry cooperating variable resistance matrices 125 and 130 as in the previous embodiments of FIGS. 3, 6, 8 and 9. The jaw embodiment of FIGS. 11 and 12 differs in that it is adapted for "one-step" welding and transection of the engaged tissue.

In FIGS. 11 and 12, of jaw structure 200 has an opening-closing mechanism that is capable of applying very high compressive forces on tissue on the basis of cam mechanisms with a reciprocating "I"-beam member 240, wherein jaw closing occurs contemporaneous with Rf energy delivery. Further, the slidable "I"-beam member 240 and the exterior jaw surfaces provide cam surfaces (i) for moving the jaw assembly to the (second) closed position to apply very high compressive forces, and (ii) for moving the jaws toward the (first) open position to apply substantially high opening forces for dissecting tissue. This feature allows the surgeon to insert the tip of the closed jaws into a dissectable tissue plane—and thereafter open the jaws to apply such dissecting forces against tissues. Many prior art instruments are spring-loaded toward the open position and may not be useful for dissecting tissue.

In the embodiment illustrated in FIGS. 11 and 12, the reciprocating "I"-beam member 240 is actuatable from the handle (not shown) of the instrument by any suitable mechanism, such as a lever arm, that is coupled to a proximal end of member 240. The distal end portion 242 of reciprocating "I"-beam member 240 carries first (lower) and second (upper) continuous laterally-extending flange elements 244A and 244B that are coupled by an intermediate transverse element 245. The flange elements 244A and 244B slide in a recessed slot portion 246 in each of the upper and lower jaws (see FIGS. 12) to close the jaws and wherein the sliding contact of the lateral edges of flanges 244A and 244B and the side of the recessed slot 246 function to prevent lateral flexing of the jaws. The transverse element 245 and blade edge 250 slide within channels 252 (collectively) in the paired first and second jaws 212A and 212B to thereby open and close the jaws. The transverse element 245 is adapted to transect tissue captured between the jaws with a sharp leading blade edge 250 (FIG. 11). In the embodiment, the "I"-beam 240 also is adapted to provide electrosurgical functionality as it transects tissue and has a polarity that matches that of the jaw bodies 232A and 232B which it slidably contacts. The jaw structure of 200 of FIGS. 11 and 12 is described in more complete detail in co-pending U.S. patent application Ser. No. 10/079,728 filed Feb. 19, 2002 entitled Electrosurgical Systems and Techniques for Sealing Tissue, and U.S. patent application Ser. No. 10/340,144 filed Jan. 10, 2003 entitled Jaw Structure for Electrosurgical Instrument and Method of Use, which are incorporated herein by this reference.

Still referring to FIGS. 11 and 12, the first and second jaws 212A and 212B close about an engagement plane 255 wherein the tissue-engaging surface layers 224A and 224B that contact and deliver energy to engaged tissue T as described above. The jaws can have any suitable length with teeth or serrations 256 for gripping tissue (FIG. 11). One preferred embodiment of FIG. 11 provides such teeth 156 at an inner portion of the jaws along channels 248 thus allowing for substantially smooth engagement surface layers 224A and 224B laterally outward of the tissue-gripping elements. The axial length of jaws 212A and 212B indicated at can be any suitable length depending on the anatomic structure targeted for transection and sealing and typically will range from about 10 mm. to 50 mm. The jaw assembly can apply very high compression over much longer lengths, for example up to about 200 mm., for resecting and sealing organs such as a lung or liver. Other embodiments of the invention provide jaw assemblies configured for use with surgical instruments known in the art used in micro-surgeries. In these and related embodiments the jaw length can be about 5.0 mm or less.

Figure 13:
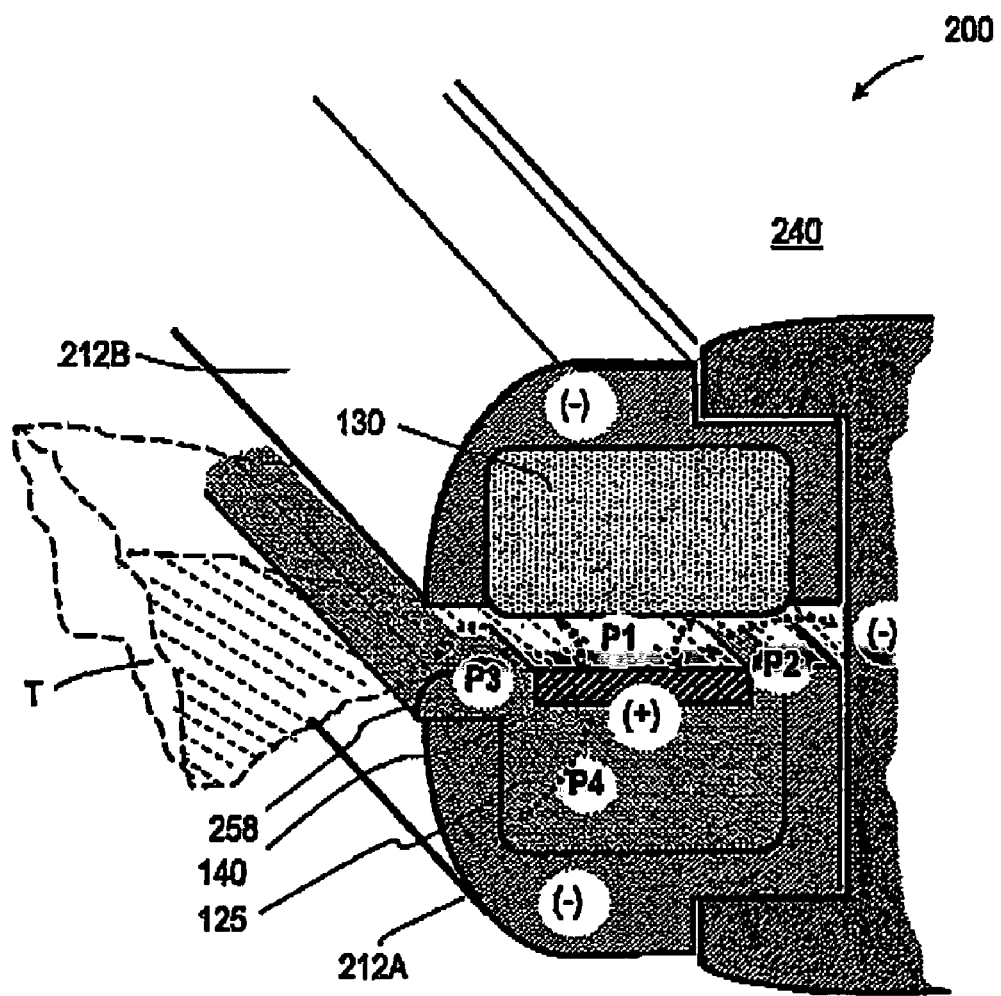
FIG. 13 is an enlarged sectional view of a portion the jaw structure of FIGS. 11-12 showing the potential current paths in engaged tissue and the variable impedance 3D matrix bodies during operation.

In FIGS. 11 and 12, it can be seen that the lower jaw 212A has a variable resistance matrix 125 that has an edge portion 258 that (optionally) extends laterally over the outer edge of the jaw body 232A. This matrix feature has been found useful in modulating Rf energy density in the margin of the treated tissue to create distinct region between welded tissue and unaffected tissue. Also, the upper jaw's matrix 130 is positioned to extend slightly outward (dimension 262) from the upper jaw body 232B. FIG. 13 illustrates that the jaw structure 200 of FIGS. 11 and 12 provides the multiplicity of flow paths P1-P4 as described previously in FIGS. 10A-10D. In all other electrosurgical aspects, the jaw structure 200 and variable resistance matrices of FIGS. 11 and 12 function as described above with reference to FIGS. 3, 6, 8, 9 and 10A-10D.

Figure 14A:
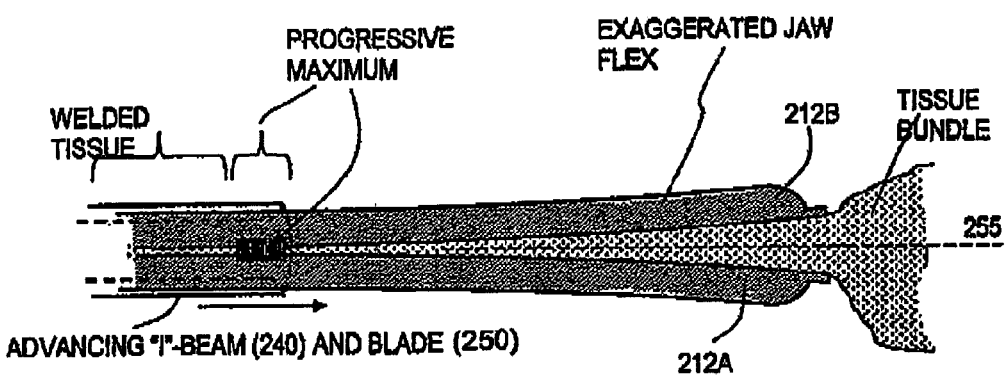
FIGS. 14A-14C are schematic sectional views of the jaw structure of FIGS. 11-13 with elongate jaws progressively engaging, welding and transecting a tissue bundle.
Figure 14B:
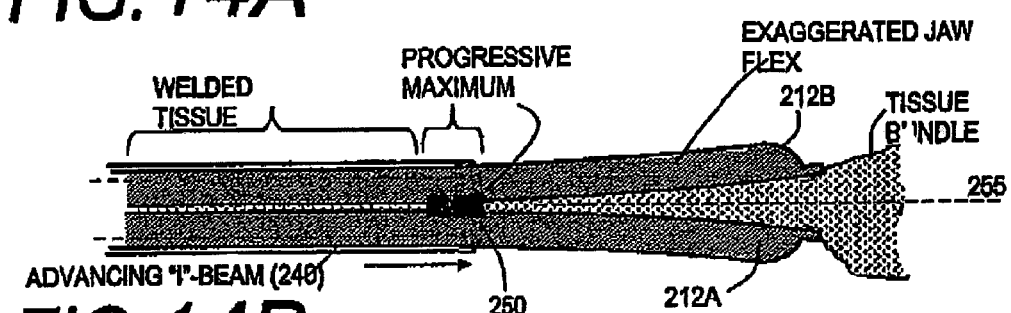
Figure 14C:
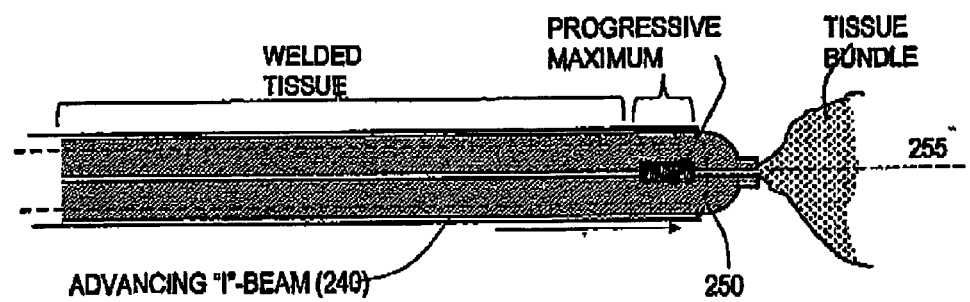

Of particular interest, FIGS. 14A-14C graphically illustrate the one-step sealing and transection method of the invention. When using elongated jaws in a small diameter instrument, the issue of jaw flexure when clamping thick tissue bundles typically creates difficulties for both sealing and transection. The jaw structure 200 of FIGS. 11 and 12 solve such problems by applying Rf energy contemporaneously with jaw closure. Initial Rf energy delivery will begin to dehydrate the engaged tissue T thus making it possible to compress the tissue to a thin membrane. At the same time, the matrices 125 and 130 will modulate Rf ohmic heating axially along the length of the jaws to thereby insure that thin treated tissue regions in the proximal jaw are not being ohmically heated while more distal regions of the engaged tissue are receiving maximal ohmic heating. All the while, each tissue region containing a different tissue type will receive the optimal Rf energy density based on impedance matching with the adjacent region of a variable impedance matrix.

In FIGS. 14A-14C, the jaws 212A and 212B are shown with a greatly exaggerated flex characteristics to illustrate, in effect, a method of the invention. The "I"-beam 240 can compress the tissue T dramatically as it is progressively welded. Thus a very small jaw structure 200 in a 5 mm. diameter device can chomp down on, weld and transect very thick tissue bundles, that are initially up to ½ inch or more. The highest ohmic heating progresses in a "front" across the tissue and is automatically modulated by the variable impedance matrices 125 and 130 and series-parallel circuitry as described above. The jaw structure 200 further allows the surgeon tactile feedback of the tissue welding process as the advancement of the "I"-beam" 240 indicates that the tissue is welded. This inventive method for welding tissue can be most accurately summarized as the microscale modulation of ohmic active heating in engaged tissue as depicted in FIGS. 10A-10D combined with the progressive macroscale application of ohmic heating as in FIGS. 14A-14C as the blade 245 transects the engaged tissue. The one-step welding and transecting functionality is provided by the high compression "I"-beam for jaw closure and tissue transection together with the cooperating variable impedance component 125 and 130 of the jaw structure.

Figure 15:
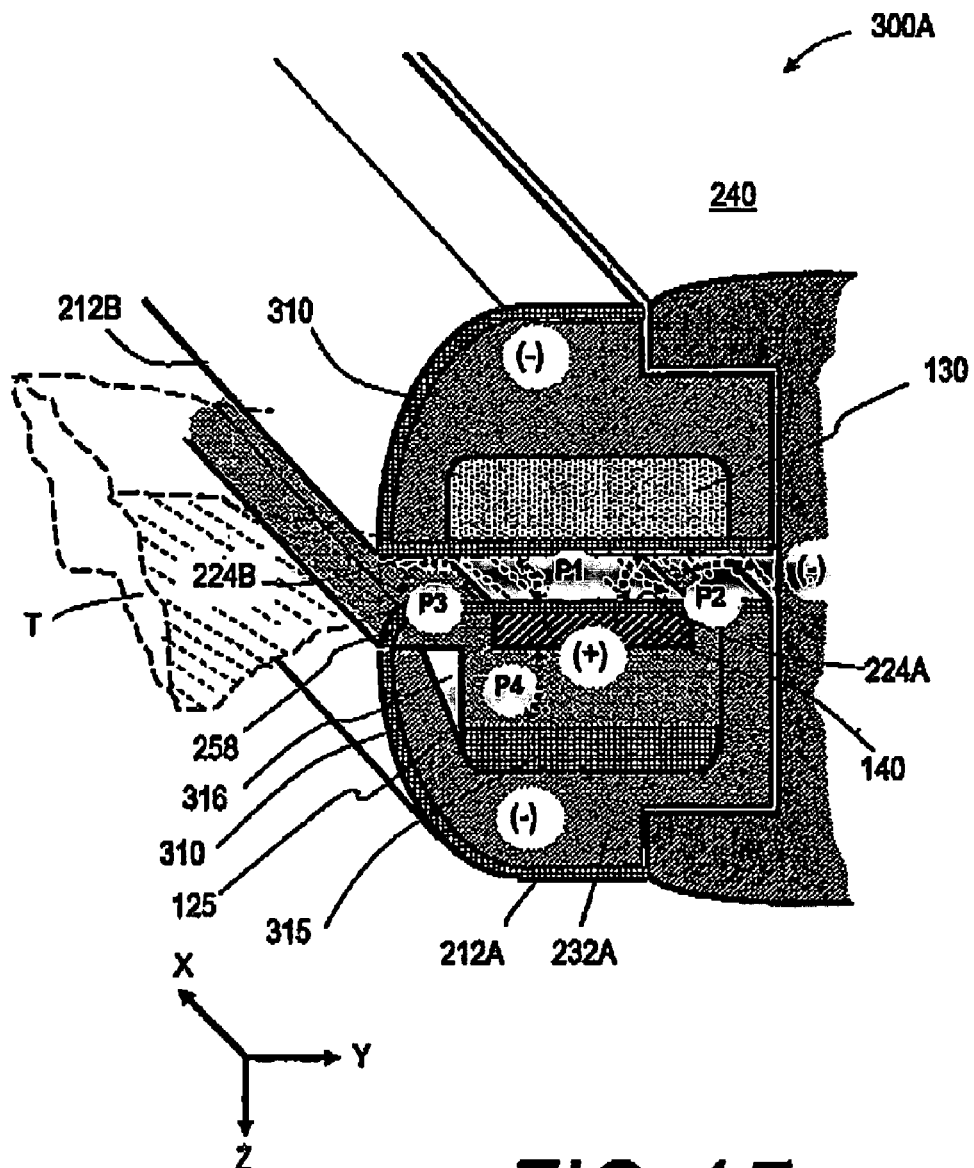
FIG. 15 is a sectional perspective view of a portion an alternative jaw structure with capacitive components combined with variable impedance matrix bodies.

Now turning to FIG. 15, an alternative embodiment of jaw structure 300A is shown that carries the same variable impedance matrices 125 and 130 as in FIGS. 11 and 12. The upper and lower jaws 212A and 212B carry matrices 125 and 130 that function largely as in the previous embodiments of FIGS. 11-13. The jaw structure 300A differs in that the opposing engagement surfaces 224A and 224B and optionally the exterior of the jaw bodies is covered with a capacitive coating of a suitable thin polymeric material layer (e.g., silicone) indicated at 310. The polymer layer can be deposited on, and bonded to, the engagement surfaces 224A and 224B by any suitable means and have a thickness ranging from about 0.05 microns to 10 microns. It has been found that such a capacitive coating in combination with a polymeric-based variable impedance material as in matrices 125 and 130 is useful in enhancing the matrices' non-stick characteristics. In effect, the exterior capacitive coating layer comprises a second energy-modulating composition that complements the energy-modulating characteristics of the variable impedance matrix composition already described above. Thus, an embodiment of the invention comprises an electrosurgical working end that carries an energy-modulating body intermediate first and second polarity conductors in tissue-engaging surface portions of the system, wherein the energy-modulating body comprises a capacitive surface portion overlying a 3D variable impedance interior portion that collectively control an Rf energy parameter (current, voltage) applied across the tissue-engaging surface portions of the system. In operation, the actual Rf application across the tissue-engaging surfaces can be described as capacitive coupling. In operation, the jaw structure 300A provides Rf energy modulation through paths P1-P4 generally as described above.

Still referring to FIG. 15, the jaw structure 300A also carries another optional alternative feature that comprises a capacitive layer 315 at an interior of the jaw body intermediate the matrix 125 and jaw body 232A. Further, the lateral portion of the variable impedance matrix 125 is covered by electrical insulator 316. The capacitive layer 315 can comprise a low durometer polymer known in the art and it can be understood that voltage levels and slight compression of the capacitive layer 315 can cause capacitive coupling between the interior of variable impedance matrix 125 and jaw body 232A to provide a current path P4 between first polarity electrode 140 and second polarity the jaw body 232A.

Figure 16:
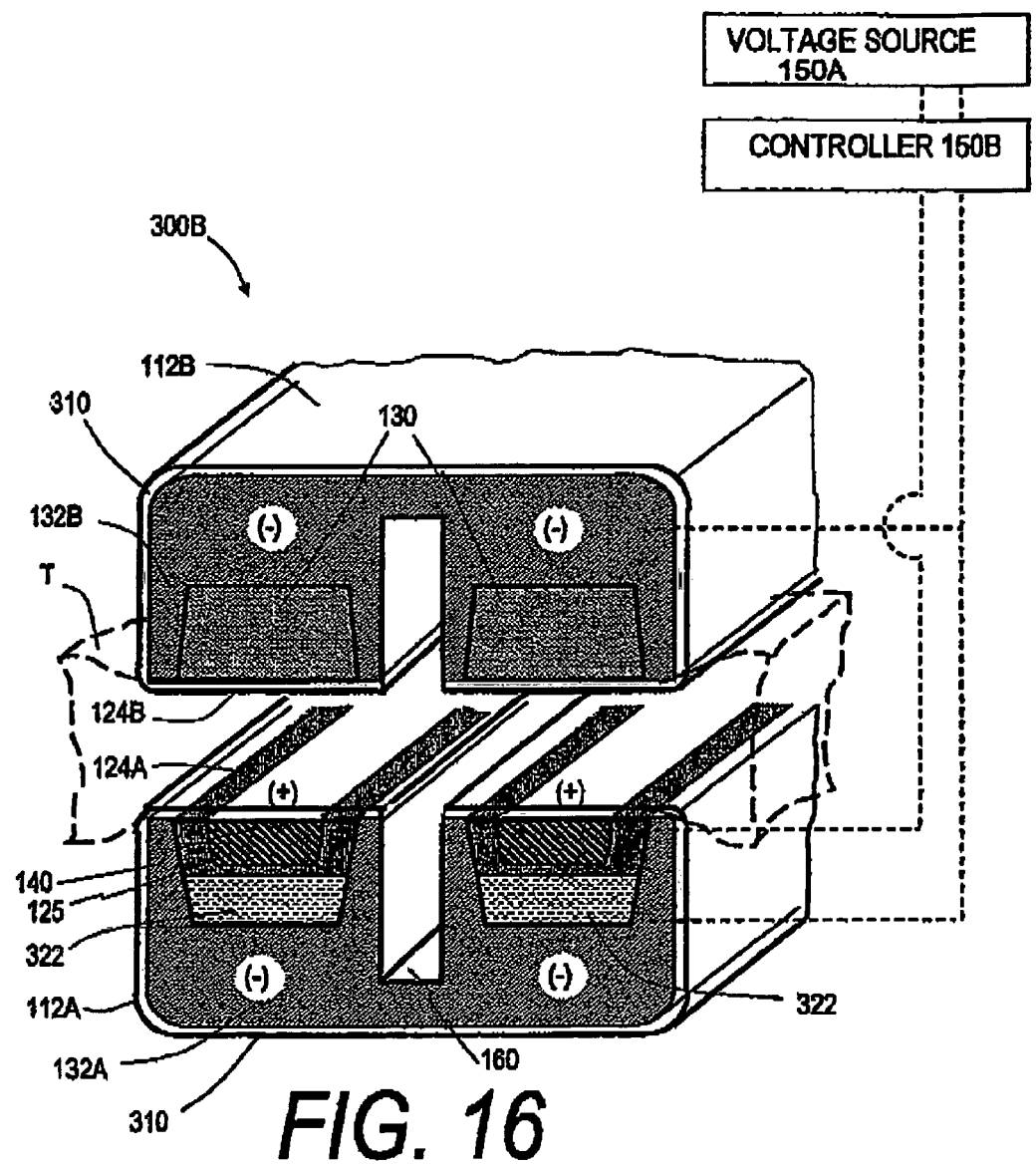
FIG. 16 is a sectional view of a portion an alternative jaw structure with negative temperature coefficient components combined with capacitive and variable impedance matrix bodies.

FIG. 16 illustrates an embodiment of an alternative jaw structure 300B that carries a capacitive layer 310 about its engagement surfaces and jaw exterior as in FIG. 15. The alternative jaw structure 300B of FIG. 16 is similar to the previously described forceps jaw of FIGS. 8 and 9, with like reference numerals. The capacitive layer 310 is depicted as a transparent layer about the entire jaws surface, except for the blade slot 160. The jaw structure differs in that the interior of the jaws carries a negative temperature coefficient matrix 322 intermediate the matrix 125 and the jaw body 232A. It can be easily understood that upon the variable impedance matrix 125 reaching a switching temperature at which the matrix reduces of terminates current flow, the negative temperature coefficient matrix 322 has a complementary switching temperature at which it allows current flow therethrough. In effect, the current path P4 then is facilitated by the use of a positive temperature coefficient variable impedance matrix body 125 exposed at the engagement surface between opposing polarity conductor portions (to respond to ohmically-heated tissue temperature) together with a corresponding negative temperature coefficient variable impedance matrix body portion 322 at an interior of the jaw to short excess voltages away from the engagement surfaces to eliminate the potential of arcs and tissue char. It should be appreciated that these capacitive features and negative temperature coefficient bodies can be provided in any of the various jaw embodiments described above.

The foregoing description of various embodiments of the invention has been presented for purposes of illustration and description. It is not intended to limit the invention to the precise forms disclosed. Many modifications, variations and refinements will be apparent to practitioners skilled in the art. Further, elements or acts from one embodiment can be readily recombined with one or more elements or acts from other embodiments to form numerous additional embodiments. Also, elements or acts from one embodiment can be readily substituted with elements or acts of another embodiment. Hence, the scope of the present invention is not limited to the specifics of the exemplary embodiment, but is instead limited solely by the appended claims.

What is claimed is:

1. An electrosurgical jaw structure comprising:
   first and second jaws defining first and second tissue engaging energy-delivery surfaces; at least one jaw comprising first and second opposing polarity portions;
   an energy-modulating body intermediate the first and second polarity portions, the energy-modulating body including a capacitive surface portion overlying a 3-dimensional variable impedance interior portion, wherein the energy-modulating body controls a selected parameter of Rf energy applied across the tissue-engaging surface portions.

2. The electrosurgical instrument of claim 1, wherein the parameter is at least one of voltage, current or impedance.

* * * * *